United States Patent
Sui et al.

(10) Patent No.: US 6,492,358 B2
(45) Date of Patent: Dec. 10, 2002

(54) β-CARBOLINE DERIVATIVES USEFUL AS INHIBITORS OF PHOSPHODIESTERASE

(75) Inventors: Zhihua Sui, Flemington, NJ (US); Mark J. Macielag, Branchburg, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/847,767

(22) Filed: May 2, 2001

(65) Prior Publication Data

US 2002/0010189 A1 Jan. 24, 2002

Related U.S. Application Data

(60) Provisional application No. 60/204,667, filed on May 17, 2000.

(51) Int. Cl.$^7$ ............... C07D 471/04; C07D 401/06; C07D 413/04; A61K 31/437; A61P 15/10
(52) U.S. Cl. ............... 514/232.8; 514/255.05; 514/256; 514/292; 544/126; 544/333; 544/405; 546/85; 546/86; 546/87
(58) Field of Search ............... 514/232.8, 255.05, 514/256, 292; 544/126, 333, 405; 546/85, 86, 87

(56) References Cited

U.S. PATENT DOCUMENTS 6,043,252 A    3/2000  Bombrun

FOREIGN PATENT DOCUMENTS

EP    1070716 A1    1/2001

OTHER PUBLICATIONS

Yang, Tsang Hsiung; Lin, Shwu Jiuan, Chung–hua Yao Hsueh Tsa Chih, 41(3), 239–46 (English) 1989.*
You, Ye–Cheng; Guo, Ming; Zhang, Xiao–Hui; Yin, Jing–Mei; Yu, Jia–You, Hecheng Huaxue, 8(1), 83–86 (Chinese) 2000.*
Jackson, Anthony Hugh; Smith, Allan, Edward, Tetrahedron, 24(1), 403–13 (English) 1968.*
Pogosyan, S. A.; Melik–Ogandzhanyan, A. S.; Paronikyan, R. G.; Noravyan, O.S. Akopyan ; N. E., Khim.–Farm.Zh., 21(6)., 678–81 (Russian) 1987.*
Grigg, R. et al., "Pictet–Spengler/Palladium Catalyzed Allenylation and Carbonylation Processes" Tetrahedron (2000), 56(35), 6585–6594.
PCT Search Report for PCT/US 01/14357 dated Mar. 19, 2002.

* cited by examiner

*Primary Examiner*—Mukund J. Shah
*Assistant Examiner*—Thomas C McKenzie
(74) *Attorney, Agent, or Firm*—Mary A. Appollina

(57) ABSTRACT

The present invention relates to novel β-carboline derivatives of the general formula

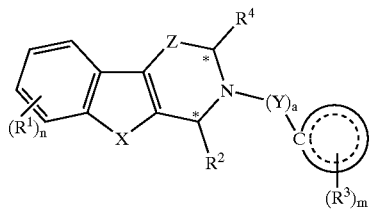

wherein all the variables are as described within the specification, useful as phosphodiesterase inhibitors. The present invention further relates to use of the described derivatives for the treatment of diseases and conditions related to PDE, for example male erectile dysfunction.

14 Claims, No Drawings

β-CARBOLINE DERIVATIVES USEFUL AS INHIBITORS OF PHOSPHODIESTERASE

CROSS REFERENCE TO RELATED APPLICATION

This application claims priority from U.S. provisional application Ser. No. 60/204,667 filed May 17, 2000, the contents of which are hereby incorporated by reference.

FIELD OF THE INVENTION

The present invention relates to novel β-carboline derivatives, useful as phosphodiesterase inhibitors. The invention further relates to synthesis of the β-carboline derivatives and intermediates used in their preparation. The present invention additionally relates to use of the described derivatives for the treatment of diseases and conditions related to PDE, for example male erectile dysfunction.

BACKGROUND OF THE INVENTION

Erectile dysfunction (ED) is defined as the inability to achieve or maintain an erection sufficiently rigid for satisfactory sexual intercourse. Currently it is estimated that approximately 7–8% of the male population suffers from some degree of ED, the equivalent of at least 20 million men in the United States alone. Since the likelihood of ED increases with age, it is projected that the incidence of this condition will rise in the future as the average age of the population increases.

Male erectile dysfunction may be the consequence of psychogenic and/or organic factors. Although ED is multifactorial, certain sub-groups within the male population are more likely to present with the symptoms of the disorder. In particular, patients with diabetes, hypertension, heart disease, and multiple sclerosis have a particularly high prevalence of ED. In addition, patients who take certain classes of drugs such as antihypertensives, antidepressants, sedatives, and anxiolytics are more prone to suffer from ED.

Treatments for ED include a variety of pharmacologic agents, vacuum devices, and penile prostheses. Among the pharmacologic agents, papaverine, phentolamine, and alprostadil are currently used in practice. These agents are only effective after direct intracavernosal or intraurethral injection, and are associated with side effects such as priapism, fibrosis, penile pain and hematoma at the injection site. Vacuum devices are a noninasive alternative treatment for ED. These devices produce an erection by creating a negative pressure around the shaft of the penis resulting in an increased blood flow into the corpus cavernosum via passive arterial dilation. Although this form of therapy is frequently successful in ED of organic origin, complaints include the lack of spontaneity and the time involved in using a mechanical device, and difficulty and discomfort with ejaculation. A variety of semi-rigid or inflatable penile prostheses have been used with some success, particularly in diabetic men. These devices are generally considered when other treatment options have failed, and are associated with an increased risk of infection and ischemia.

Recently, the phosphodiesterase V (PDEV) inhibitor, sildenafil (Viagra®) was approved by the FDA as an orally effective medication for the treatment of ED. Sildenafil, 5-[2-ethoxy-5-(4-methylpiperazin-1-ylsulphonyl)phenyl]-1-methyl-3-n-propyl-6,7-dihydro-1H-pyrazolo[4,3-d]pyrimidin-7-one and a number of related analogs and their use as antianginal agents are described in U.S. Pat. Nos. 5,250,534 and 5,346,901. The use of sildenafil and related analogs for treating male erectile dysfunction is described in PCT International Application Publication No. WO 94/28902, published Dec. 22, 1994. In clinical studies, the drug improved sexual function in about 70% of the men who suffer from ED of psychogenic or organic etiology. However, the drug showed less dramatic efficacy in patients who had undergone a radical prostatectomy, with improved erections in 43% of patients who took sildenafil versus 15% on placebo. In addition, the use of sildenafil is associated with several undesirable side effects including headache, flushing and disrupted color vision which result from nonselective effects on a variety of tissues. In spite of these shortcomings, the drug is viewed by patients as preferable to other treatments which involve the introduction of medication directly into the penis via injection, the use of an external device or a surgical procedure.

Daugan et.al, in U.S. Pat. No. 5,859,009 (EP 0740668 B1 and WO9519978) describe the synthesis of tetracyclic derivatives as inhibitors of cyclic guanosine 3',5'-monophosphate specifically phosphodiesterase, and their use in treating cardiovascular disorders. Daugan et.al., in WO97/03675 teach the use of tetracyclic derivatives for the treatment of impotence.

Bombrun et al., in WO 97/43287 describe a series of carboline derivatives, more specifically 2-(substituted alkyl carbonyl) substituted carboline derivatives and their use in treating cardiovascular disorders as inhibitors of cyclic guanosine 3,5-monophosphate, specifically phosphodiesterase.

Ellis et. al., in WO 94/28902 and EP0702555 B1 describes a series of pyrazolpyrimidinone derivatives and their use in treating erectile dysfunction. Campbell, S. F. in WO96/16657 teaches the use of bicyclic heterocyclic compounds for the treatment of impotence (pyrazolopyrimidones); while Campbell et al, in WO,96/16644 teach the use of selective cGMP PDE inhibitors for the treatment of erectile dysfunction.

Ohashi et al., in WO9745427 disclose tetracyclic pyridocarbazole derivatives having cGMP PDE inhibitory effects.

Fourtillan et. al., in WO 96/08490 A1 describe a series of carboline derivatives and their use in the treatment of diseases associated with melatonin activity disorders. Ueki et. al., in U.S. Pat. No. 5,126,448 describe pyridine and 1,2,3,4-tetrahydropyridine derivatives useful as psychotropic drugs having antianxiety effects. Atkinson et. al., in U.S. Pat. No. 3,328,412 describe 1-aryl- and 1-heteroaryl-2-acly-1,2,3,4-tetrahydro-β-carboline derivatives having long lasting analgesic properties.

Sexually stimulated penile erection results from a complex interplay of physiological processes involving the central nervous system, the peripheral nervous system, and the smooth muscle. Specifically, release of nitric oxide from the non-adrenergic, non-cholinergic nerves and endothelium activates guanylyl cyclase and increases intracellular cGMP levels within the corpus cavernosum. The increase in intracellular cGMP reduces intracellular calcium levels, resulting in trabecular smooth muscle relaxation, which, in turn, results in corporal volume expansion and compression of the sub-tunical venules leading to penile erection.

PDEV has been found in human platelets and vascular smooth muscle, suggesting a role for this enzyme in the regulation of intracellular concentrations of cGMP in cardiovascular tissue. In fact, inhibitors of PDEV have been shown to produce endothelial-dependent vasorelaxation by potentiating the increases in intracellular cGMP induced by nitric oxide. Moreover, PDEV inhibitors selectively lower the pulmonary arterial pressure in animal models of congestive heart failure and pulmonary hypertension. Hence in addition to their utility in ED, PDEV inhibitors would likely be of therapeutic benefit in conditions like heart failure, pulmonary hypertension, and angina.

Agents that increase the concentration of cGMP in penile tissue, either through enhanced release or reduced breakdown of cGMP, are expected to be effective treatments for ED. The intracellular levels of cGMP are regulated by the enzymes involved in its formation and degradation, namely the guanylate cyclases and the cyclic nucleotide phosphodiesterases (PDEs). To date, at least nine families of mammalian PDEs have been described, five of which are capable of hydrolyzing the active, cGMP, to the inactive, GMP, under physiological conditions (PDEs I, II, V, VI, and IX). PDE V is the predominant isoform in human corpus cavernosum. Inhibitors of PDEV, therefore, would be expected to increase the concentration of cGMP in the corpus cavernosum and enhance the duration and frequency of penile erection.

Additionally, selective PDE inhibitors are known to be useful in the treatment of various disorders and conditions including male erectile dysfunction (ED), female sexual arousal dysfunction, female sexual dysfunction related to blood flow and nitric oxide production in the tissues of the vagina and clitoris, premature labor, dysmenorrhea, cardiovascular disorders, atherosclerosis, arterial occlusive disorders, thrombosis, coronary rest stenosis, angina pectoris, myocardial infarction, heart failure, ischemic heart disorders, hypertension, pulmonary hypertension, asthma, intermittent claudication and diabetic complications.

Accordingly, it is an object of the invention to identify compounds which increase the concentration of cGMP in penile tissue through the inhibition of phosphodiesterases, specifically PDEV. It is another object of the invention to identify compounds which are useful for the treatment of sexual dysfunction, particularly erectile dysfunction and/or impotence in male animals and sexual dysfunction in female animals. Still another object of the invention is to identify methods for treating sexual dysfunction, especially erectile dysfunction, using the compounds of the present invention.

It is another object of the invention to identify compounds which are useful for the treatment of conditions of disorders mediated by PDEV, such as male erectile dysfunction, female sexual dysfunction, cardiovascular disorders, atherosclerosis, arterial occlusive disorders, thrombosis, coronary rest stenosis, angina pectoris, myocardial infarction, heart failure, ischemic heart disorders, hypertension, pulmonary hypertension, asthma, intermittent claudication or diabetic complications.

We now describe a series of β-carboline derivatives with the ability to inhibit phosphodiesterase type V in enzyme assays and increase the concentration of cGMP in cavernosal tissue in vitro.

SUMMARY OF THE INVENTION

The present invention provides novel β-carboline derivative compounds useful as phosphodiesterase inhibitors. More particularly, the present invention is directed to compounds of the general formula (I):

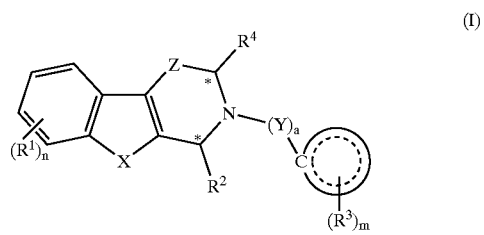

wherein $R^1$ is independently selected from the group consisting of halogen, nitro, hydroxy, $C_1$–$C_8$alkyl, $C_1$–$C_8$alkoxy, —$NH_2$, —$NHR^A$, —$N(R^A)_2$, —O—$R^A$, —C(O)$NH_2$, —C(O)$NHR^A$, —C(O)N$(R^A)_2$, —NC(O)—$R^A$, —$SO_2NHR^A$, —$SO_2N(R^A)_2$, phenyl (optionally substituted with 1 to 3 $R^B$) and heteroaryl (optionally substituted with 1 to 3 $R^B$);

where each $R^A$ is independently is independently selected from the group consisting of $C_1$–$C_8$alkyl, aryl (optionally substituted with 1 to 3 $R^B$), $C_1$–$C_8$aralkyl (optionally substituted with 1 to 3 $R^B$) and heteroaryl (optionally substituted with 1 to 3 $R^B$);

where each $R^B$ is independently selected from the group consisting of halogen, hydroxy, nitro, cyano, $C_1$–$C_8$alkyl, $C_1$–$C_8$alkoxy, $C_1$–$C_8$alkoxycarbonyl, carboxy$C_1$–$C_8$alkyl, $C_1$–$C_8$alkylsulfonyl, trifluoromethyl, trifluoromethoxy, amino, acetylamino, di($C_1$–$C_8$alkyl)amino, di($C_1$–$C_8$alkyl)amino$C_1$–$C_8$alkoxy, di($C_1$–$C_8$alkyl)aminoacetyl$C_1$–$C_8$alkyl, di($C_1$–$C_8$alkyl)aminoacetylamino, carboxy$C_1$–$C_8$alkylcarbonylamino, hydroxy$C_1$–$C_8$alkylamino, $NHR^A$ $N(R^A)_2$ and heterocycloalkyl$C_1$–$C_8$alkoxy;

n is an integer from 0 to 4;

X is selected from the group consisting of O, S and $NR^D$;

where $R^D$ is selected from the group consisting of hydrogen, hydroxy, —$OR^A$, $C_1$–$C_8$alkyl (wherein the alkyl is optionally substituted with one to three substituent independently selected from halogen, carboxy, amino, $C_1$–$C_8$alkylamino, di($C_1$–$C_8$alkyl)amino, $C_1$–$C_8$alkoxycarbonyl, heteroaryl or heterocycloalkyl), heteroaryl and heteroarylcarbonyl (wherein the heteroaryl may be optionally substituted with phenyl or substituted phenyl, where the phenyl substituents are one to three $R^B$);

$R^2$ is selected from the group consisting of $C_5$–$C_{10}$alkyl (optionally substituted with 1 to 3 $R^C$), aryl (optionally substituted with 1 to 3 $R^B$), heteroaryl (optionally substituted with 1 to 3 $R^B$) and heterocycloalkyl (optionally substituted with 1 to 3 $R^B$);

where each $R^C$ is independently selected from the group consisting of halogen, hydroxy, nitro, $NH_2$, $NHR^A$ and $N(R^A)_2$;

Z is selected from the group consisting of $CH_2$, CHOH and C(O); provided that when Z is CHOH or C(O), then X is NH;

$R^4$ is selected from the group consisting of hydrogen, hydroxy, carboxy, $C_1$–$C_6$alkylcarbonyl, $C_1$–$C_6$alkoxylcarbonyl, di($C_1$–$C_8$alkyl)aminoalkoxycarbonyl, di($C_1$–$C_8$alkyl)amino$C_1$–$C_8$alkylaminocarbonyl, and —$COR^F$;

where $R^F$ is selected from the group consisting of $C_1$–$C_8$alkyl, $NH_2$, $NHR^A$, $NR^A_2$, —$C_1$–$C_8$alkyl—$NH_2$, —$C_1$–$C_8$alkyl-$NHR^A$, —$C_1$–$C_8$alkyl-$NR^A{}_2$ and —NH—$C_1$–$C_8$alkyl-$NR^A{}_2$;

a is an integer from 0 to 1;

Y is selected from the group consisting of $CH_2$, C(O), C(O)O, C(O)—NH and $SO_2$;

is selected from the group consisting of naphthyl, heteroaryl and heterocycloalkyl;

m is an integer from 0 to 2;

$R^3$ is independently selected from the group consisting of halogen, nitro, $C_1$–$C_8$alkyl, $C_1$–$C_8$alkoxy, trifluoromethyl, trifluoromethoxy, phenyl (optionally substituted with 1 to 3 $R^B$), phenyisulfonyl, naphthyl, $C_1$–$C_8$aralkyl, heteroaryl (optionally substituted with 1 to 3 $R^B$), $NH_2$, $NHR^A$ and $N(R^A)_2$;

provided that when

is 2-furyl or 2-thienyl, then m is an integer from 1 to 2; and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating sexual dysfunction, for example, male erectile dysfunction, impotence, female sexual dysfunction, for example female sexual arousal dysfunction, female sexual dysfunction related to blood flow and nitric oxide production in the tissues of the vagina and clitoris, premature labor and/or dysmenorrhea in a subject in need thereof comprising administering to the subject a therapeutically effective amount of any of the compounds or pharmaceutical compositions described above.

An example of the invention is a method for increasing the concentration of cGMP in penile tissue through the inhibition of phosphodiesterases, specifically PDEV, in a male subject in need thereof comprising administering to the subject an effective amount of any of the compounds or pharmaceutical compositions described above.

Further exemplifying the invention is a method of producing endothelial-dependent vasorelaxation by potentiating the increases in intracellular cGMP induced by nitric oxide in a subject in need thereof comprising administering to the subject an effective amount of any of the compounds or pharmaceutical compositions described above.

Further illustrating the invention is a method of treating a condition selected from the group consisting of male erectile dysfunction (ED), impotence, female sexual dysfunction, female sexual arousal dysfunction, female sexual dysfunction related to blood flow and nitric oxide production in the tissues of the vagina and clitoris, premature labor, dysmenorrhea, cardiovascular disorders, atherosclerosis, arterial occlusive disorders, thrombosis, coronary rest stenosis, angina pectoris, myocardial infarction, heart failure, ischemic heart disorders, hypertension, pulmonary hypertension, asthma, intermittent claudication and diabetic complications in a subject in need thereof comprising administering to the subject a therapeutically effective amount of any of the compounds or pharmaceutical compositions described above.

An example of the invention is the use of any of the compounds described above in the preparation of a medicament for: (a) treating sexual dysfunction, especially male erectile dysfunction, (b) treating impotence, (c) increasing the concentration of cGMP in penile tissue through inhibition of phosphodiesterase, especially PDEV and/or (d) treating a condition selected from the group consisting of premature labor, dysmenorrhea, cardiovascular disorders, atherosclerosis, arterial occlusive disorders, thrombosis, coronary rest stenosis, angina pectoris, myocardial infarction, heart failure, ischemic heart disorders, hypertension, pulmonary hypertension, asthma, intermittent claudication and diabetic complications in a subject in need thereof.

DETAILED DESCRIPTION OF THE INVENTION

The present invention provides novel β-carboline derivatives useful for the treatment of sexual dysfunction, particularly male erectile dysfunction (ED). Although the compounds of the present invention are useful primarily for the treatment of male sexual dysfunction or erectile dysfunction, they may also be useful for the treatment of female sexual dysfunction, for example female sexual arousal dysfunction, female sexual dysfunction related to blood flow and nitric oxide production in the tissue of the vagina and clitoris, and of premature labor and dysmenorrhea.

More particularly, the compounds of the present invention are of the formula (I):

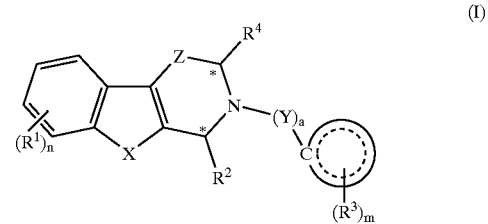

wherein all variables are as defined above.

Preferably, n is 0. Preferably, m is an integer from 0 to 1.

In an embodiment of the present invention X is selected from S or $NR^D$, wherein $R^D$ is selected from the group consisting of hydrogen, halo$C_1$–$C_6$alkyl, di($C_1$–$C_4$alkyl)amino$C_1$–$C_6$alkyl, heteroaryl, heteroaryl$C_1$–$C_4$alkyl, heterocycloalkyl$C_1$–$C_4$alkyl, carboxy$C_1$–$C_4$alkyl, $C_1$–$C_4$alkoxycarbonyl$C_1$–$C_4$alkyl and heteroarylcarbonyl; wherein the heteroaryl is further optionally substituted with phenyl or substituted phenyl, wherein the substituents on the phenyl are one to two independently selected from $R^B$; and wherein each $R^B$ is independently selected from the group consisting of halogen, nitro, $C_1$–$C_4$alkyl, $C_1$–$C_4$alkoxy, trifluoromethyl, trifluoromethoxy, amino and di($C_1$–$C_4$alkyl)amino. Preferably, X is selected from S or $NR^D$, where $R^D$ is selected from the group consisting of hydrogen, di(methyl)aminoethyl, di(methyl)amino-n-propyl, di(ethyl)aminoethyl, di(ethyl)amino-n-butyl, N-pyrrolidinylethyl, N-morpholinylethyl, 2-pyridylmethyl, 4-pyridylmethyl, 5-(4-methylphenyl)-2-pyrimidinyl, carboxymethyl, carboxyethyl, 4-chloro-n-butyl, 2-(5-(3-trifluoromethylphenyl)furyl)carbonyl, 2-(5-(3-nitrophenyl)furyl)carbonyl, methoxycarbonylmethyl, methoxycarbonylethyl and 2-benzoxazolyl. More preferably, X is $NR^D$, where $R^D$ is selected from the group consisting of hydrogen, di(methyl)aminoethyl, 4-pyridylmethyl, 2-pyridylmethyl, N-morpholinylethyl, carboxyethyl, carboxymethyl, di(ethyl)aminoethyl, N-pyrrolidinylethyl and 5-(4-methylphenyl)-2-pyrimidinyl. Most preferably, X is $NR^D$, where $R^D$ is selected from the group consisting of hydrogen, di(methyl)aminoethyl, N-morpholinylethyl, carboxymethyl and N-pyrrolidinylethyl;

Preferably, Z is selected from the group consisting of $CH_2$ and $C(O)$; provided that when Z is $C(O)$, then X is NH.

Preferably, Y is selected from the group consisting of $C(O)$, $SO_2$ and $CH_2$. More preferably, Y is selected from the group consisting of $C(O)$ and $CH_2$. Most preferably, Y is $C(O)$.

In an embodiment of the present invention

is selected from the group consisting of naphthyl and heteroaryl. Preferably,

is selected from the group consisting of naphthyl, 2-pyrimidinyl, 2-furyl, 3-furyl, 2-benzofuryl, 2-theinyl, 2-benzothienyl, 2-benzothiazolyl, 2-benzoxazolyl, 2-benzimidazolyl, 4-thiazolyl, 2-thiazolyl, 3-pyrazolyl, 4-pyrazolyl, 5-pyrazolyl, 3-(1,2,5-triazolyl), 4-isoxazolyl, 2-pyridyl and 3-pyridyl. More preferably,

is selected from the group consisting of naphthyl, 2-pyrimidinyl, 2-furyl, 2-benzofuryl, 2-thienyl, 2-benzothienyl, 2-benzothiazolyl, 2-benzoxazolyl, 2-thiazolyl, 4-thiazolyl and 2-pyridyl. Most preferably,

is selected from the group consisting of 2-pyrimidinyl, 2-furyl, 2-benzofuryl, 2-benzoxazolyl, 2-thiazolyl and 2-pyridyl.

In an embodiment of the present invention, $R^2$ is selected from the group consisting of 3,4-methylenedioxyphenyl, 3,4-(difluoro)methylenedioxyphenyl, 2,3-dihydrobenzofuryl, 2,3-dihydrobenzo-[1,4]-dioxin-6-yl, pyridyl, phenyl and substituted phenyl; wherein the phenyl substituents are one to two substituents independently selected from halogen, $C_1$–$C_4$alkyl, $C_1$–$C_4$alkoxy, trifluoromethyl, cyano, nitro, $C_1$–$C_4$alkoxycarbonyl, di($C_1$–$C_4$alkyl)amino or di($C_1$–$C_4$alkyl)amino$C_1$–$C_4$alkoxy. Preferably, $R^2$ is selected from the group consisting of phenyl, 3,4-methylenedioxyphenyl, 3,4-(difluoro)methylenedioxyphenyl, 2,3-dihydrobenzofuryl, 2,3-dihydrobenzo-[1,4]-dioxin-6-yl, 4-pyridyl, 3-pyridyl, 4-cyanophenyl, 3-nitrophenyl, 4-nitrophenyl, 4-trifluoromethylphenyl, 4-methoxyphenyl, 3,4-dimethylphenyl, 3,5-dimethylphenyl, 3,4-dimethoxyphenyl, 3-trifluoromethyl-4-chlorophenyl, 3,4-dichlorophenyl, 4-chlorophenyl, 4-methoxycarbonylphenyl, 3,4-dimethoxyphenyl, 4-(dimethylamino)phenyl and 4-(N-(3-dimethylamino)-n-propoxy)phenyl. More preferably, $R^2$ is selected from the group consisting of 3,4-methylenedioxyphenyl, 2,3-dihydrobenzofuryl and 2,3-dihydrobenzo-[1,4]-dioxin-6-yl. Most preferably, $R^2$ is selected from the group consisting of 3,4-methylenedioxyphenyl and 2,3-dihydrobenzofuryl.

Preferably, $R^4$ is selected from the group consisting of hydrogen, carboxy, $C_1$–$C_4$alkoxycarbonyl, di($C_1$–$C_4$alkyl)amino$C_1$–$C_4$alkoxycarbonyl and di($C_1$–$C_4$alkyl)amino$C_1$–$C_4$alkylaminocarbonyl. More preferably, $R^4$ is selected from the group consisting of hydrogen, carboxy, dimethylaminoethoxycarbonyl, dimethylaminoethylaminocarbonyl and methoxycarbonyl. Most preferably, $R^4$ is hydrogen.

In an embodiment of the present invention, $R^3$ is independently selected from the group consisting of halogen, nitro, $C_1$–$C_4$alkyl, $C_1$–$C_4$alkoxy, trifluoromethyl, $C_1$-$C_4$aralkyl, pyrazinyl, pyridyl, halogen substituted pyridyl, dimethyl substituted imidazolyl, phenyl, phenyisulfonyl and substituted phenyl; wherein the substituents on the phenyl are one or more substituents independently selected from halogen, hydroxy, $C_1$–$C_4$alkyl, $C_1$–$C_4$alkoxy, trifluoromethyl, trifluoromethoxy, nitro, amino, acetylamino, $C_1$–$C_4$alkylsulfonyl, carboxy$C_1$–$C_4$alkylcarbonylamino, hydroxy$C_1$–$C_4$alkylamino, di($C_1$–$C_4$alkyl)amino$C_1$–$C_4$alkoxy, di($C_1$–$C_4$alkyl)aminoacetylamino or heterocycloalkyl$C_1$–$C_4$alkoxy. Preferably, $R^3$ is independently selected from the group consisting of chloro, bromo, methyl, n-propyl, t-butyl, methoxy, trifluoromethyl, nitro, phenyl, benzyl, phenylsulfonyl, 4-hydroxyphenyl, 4-chlorophenyl, 4-methylphenyl, 3,4-dimethoxyphenyl, 3-trifluoromethylphenyl, 4-trifluoromethylphenyl, 5-trifluoromethylphenyl, 4-methoxyphenyl, 2-nitrophenyl, 3-nitrophenyl, 4-nitrophenyl, 3-aminophenyl, 4-aminophenyl, 2-nitro-4-chlorophenyl, 2-nitro-4-methylphenyl, 2-nitro-4-methylsulfonylphenyl, 3-acetylaminophenyl, 4-acetylaminophenyl, 4-(3-carboxy-n-propyl)carbonylaminophenyl, 2-chloro-5-trifluoromethylphenyl, 4-(4-hydroxy-n-butyl)aminophenyl, 2-(dimethylamino)acetylaminop the group consisting of bromo, t-butyl, methoxy, trifluoromethyl, nitro, phenyl, 4-chlorophenyl, 3,4-dimethoxyphenyl, 3-trifluoromethylphenyl, 4-methylphenyl, 4-methoxyphenyl, 2-nitrophenyl, 3-nitrophenyl, 4-nitrophenyl, 3-aminophenyl, 2-nitro-4-chlorophenyl, 2-nitro-4-methylphenyl, 2-nitro-4-methylsulfonylphenyl, 4-(3-carboxy-n-propyl)carbonylaminophenyl, 2-chloro-5-trifluoromethylphenyl, 4-hydroxy-n-butyl)aminophenyl, 2-2-(dimethylamino)acetylaminophenyl, 4-pyrazinyl 2-pyridyl and 2,3-dimethyl-3H-imidazol-4-yl. Most preferably, $R^3$ is selected from the group consisting of t-butyl, methoxy, nitro, phenyl, 4-chlorophenyl, 4-methylphenyl, 4-methoxyphenyl, 3,4-dimethoxyphenyl, 3-trifluoromethylphenyl, 2-nitrophenyl, 3-nitrophenyl, 4-nitrophenyl, 3-aminophenyl, 2-nitro-4-methylsulfonylphenyl, 2-(dimethylamino)acetylaminophenyl, 2-pyridyl and 2,3-dimethyl-3H-imidazol-4-yl.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methyinitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

As used herein, unless otherwise noted, "halogen" shall mean chlorine, bromine, fluorine and iodine.

The term "alkyl", whether used alone or as part of a substituent group, shall mean straight or branched chain alkanes of one to ten carbon atoms, or any number within this range. For example, alkyl radicals include, methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl and 2-methylpentyl.

The term "alkoxy" shall denote an oxygen ether radical of the above described straight or branched chain alkyl group. For example, alkoxy radicals include methoxy, ethoxy, n-propoxy, n-butoxy, sec-butoxy, tert-butoxy, and the like.

The term "aryl" indicates an aromatic groups such as phenyl, naphthyl, and the like.

The term "aralkyl" denotes an alkyl group substituted with an aryl group. For example, benzyl, phenylethyl, and the like.

The term "heteroaryl" as used herein represents a stable five or six membered monocyclic aromatic ring system containing one to three heteroatoms independently selected from N, O or S; and any nine or ten membered bicyclic aromatic ring system containing carbon atoms and one to four heteroatoms independently selected from N, O or S. The heteroaryl group may be attached at any heteroatom or carbon atom which results in the creation of a stable structure. Examples of heteroaryl groups include, but are not limited to pyridyl, pyrimidinyl, thienyl, furyl, imidazolyl, isoxazolyl, oxazolyl, pyrazolyl,pyrazinyl, pyrrolyl, thiazolyl, thiadiazolyl, triazolyl, benzimidazolyl, benzofuranyl, benzothienyl, benzisoxazolyl, benzoxazolyl, indazolyl, indolyl, benzothiazolyl, benzothiadiazolyl, benzotriazolyl, quinolinyl or isoquinolinyl. Particularly preferred heteroaryl groups include pyridyl, pyrazolyl, furyl, thiazolyl, thienyl, imidazolyl, isoxazolyl, pyrazinyl, pyrimidinyl, triazolyl, benzofuryl, benzothienyl, benzimidazolyl, benzothiazolyl and benzoxazolyl.

The term "cycloalkyl" as used herein represents a stable three to eight membered monocyclic ring structure consisting of saturated carbon atoms. Suitable examples include cyclopropyl, cyclobutyl, cyclopentyl, cyclohexyl, cycloheptyl and cyclooctyl.

The term "heterocycloalkyl" represents a stable saturated or partially unsaturated, three to eight membered monocyclic ring structure containing carbon atoms and one to four, preferably one to two, heteroatoms independently selected from N, O or S; and any stable saturated, partially unsaturated or partially aromatic, nine to ten membered bicyclic ring system containing carbon atoms and one to four heteroatoms independently selected from N, O or S. The heterocycloalkyl may be attached at any carbon atom or heteroatom which results in the creation of a stable structure. Suitable examples of heterocycloalkyl groups include pyrrolidinyl, pyrazolidinyl, piperidinyl, piperazinyl, morpholinyl, dithianyl, trithianyl, dioxolanyl, dioxanyl, thiomorpholinyl, 3,4-methylenedioxyphenyl, 2,3-dihydrobenzofuryl, 2,3-dihydrobenzo-[1,4]-dioxin-6-yl, 2,3-dihydro-furo[2,3-b]pyridyl, 1,2-(methylenedioxy) cyclohexane, and the like. Particularly preferred heterocycloalkyl groups include pyrrolidinyl, morpholinyl, 3,4-methylenedioxyphenyl, 2,3-dihydrobenzofuryl and 2,3-dihydrobenzo-[1,4]-dioxin-6-yl.

As used herein, the notation "*" shall denote the presence of a stereogenic center.

Under standard nomenclature used throughout this disclosure, the terminal portion of the designated side chain is described first, followed by the adjacent functionality toward the point of attachment. Thus, for example, a "phenyl$C_1$–$C_6$ alkylaminocarbonyl$C_1$–$C_6$alkyl" substituent refers to a group of the formula

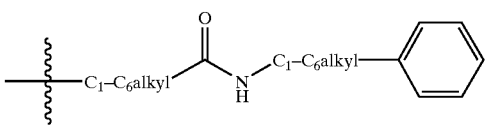

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein. It is further intended that when n or m is >1, the corresponding $R^1$ or $R^3$ substituents may be the same or different.

The term "sexual dysfunction" as used herein, includes male sexual dysfunction, male erectile dysfunction, impotence, female sexual dysfunction, female sexual arousal dysfunction and female sexual dysfunction related to blood flow and nitric oxide production in the tissues of the vagina and clitoris.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Abbreviations used in the specification, particularly the Reactions and Examples, are as follows:

| | |
|---|---|
| Cmpd # = | Compound ID Number |
| DCC = | 1,3-Dicyclohexylcarbodiimide |
| DCM = | Dichloromethane |
| DDQ = | Dichlorodicyanoquinone |
| DIC = | Diisopropylcarbodiimide |
| DIPEA = | Diisopropylethylamine |
| DMF = | N,N-Dimethylformamide |
| DMSO = | Dimethylsulfoxide |
| dppp = | 1,3-Bis(diphenylphosphino) propane |
| EDTA = | Ethylenedinitrilotetracetic acid |
| Fmoc = | 9-Fluorenylmethoxycarbonyl |
| Fmoc-NCS = | 9-fluorenylmethoxycarbonyl isothiocyanate |
| HEPES = | 2-[4-(2-Hydroxyethyl)-piperazinyl]-ethanesulfonic acid |
| LAH = | Lithium Aluminum Hydride |
| PDE = | Phosphodiesterase |
| $Pd_2dba_3$ = | Tris(dibenzylidene acetone) dipalladium (0) |
| $Pd(OAc)_2$ = | Palladium (II) Acetate |
| $Pd(PPh_3)_4$ = | Palladium tetrakis(triphenyl phosphine) |
| Ph = | Phenyl |
| PMSF = | Phenylmethane sulfonyl fluoride |
| $PPh_3$ = | Triphenyl phosphine |
| PyBop = | (1-Hydroxy-1H-benzotriazolato-O)tri-1-pyrrolidinyl phosphorous |
| PyBrop = | Bromo-tri-1-pyrridinyl phosphorous |
| SNP = | Sodium nitroprusside |
| TEA = | Triethylamine |
| TFA = | Trifluoroacetic acid |
| THF = | Tetrahydrofuran |
| TsOH = | Tosic Acid |

Compounds of formula (I) may be prepared according to the processes outlined in more detail below.

Compounds of formula (I) wherein $(Y)_a$ is C(O) may be prepared according to a process as outlined in Scheme 1.

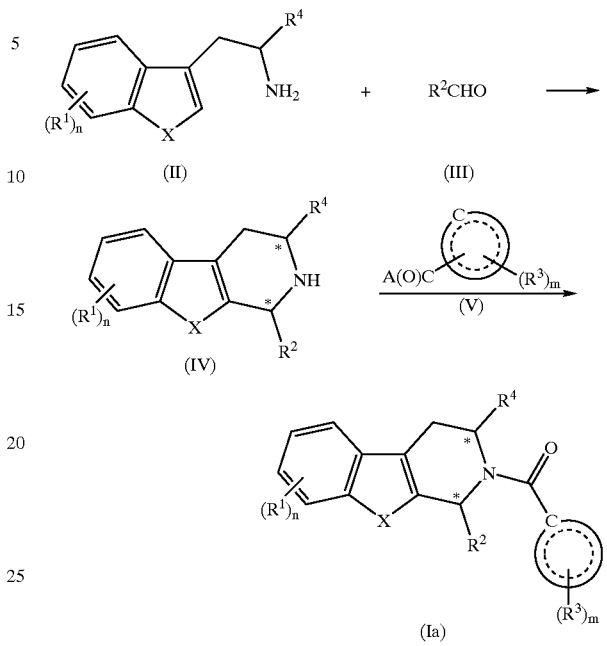

More particularly, a compound of formula (II), wherein X is O, S or NH, a known compound or compound produced by known methods, is reacted with a suitably substituted aldehyde of formula (III), in an organic solvent such as DCM, THF, toluene, and the like, in the presence of an acid catalyst such as TFA, tosic acid, and the like, to produce the corresponding tricyclic compound of formula (IV).

The compound of formula (IV) is reacted with a suitably substituted compound of formula (V), wherein A is halogen, in the presence of a base such as triethylamine (TEA), diisopropylethylamine (DIPEA), sodium carbonate and the like, in an organic solvent such as dichloromethane (DCM), N,N'-dimethylformamide (DMF), tetrahydrofuran (THF), and the like; or with a suitably substituted compound of formula (V), wherein A is hydroxy, in the presence of a coupling agent such as DCC, DIC, PyBop, PyBrop, and the like, in an organic solvent such as dichloromethane (DCM), N,N'-dimethylformamide (DMF), tetrahydrofuran (THF), and the like; to produce the corresponding compound of formula (Ia).

Alternatively, compounds of formula (I), wherein X is O, S, or NH and $(Y)_a$ is C(O) may be prepared according to a process as outlined in Scheme 2.

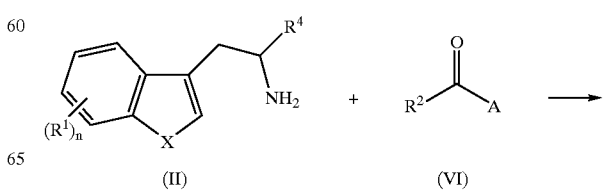

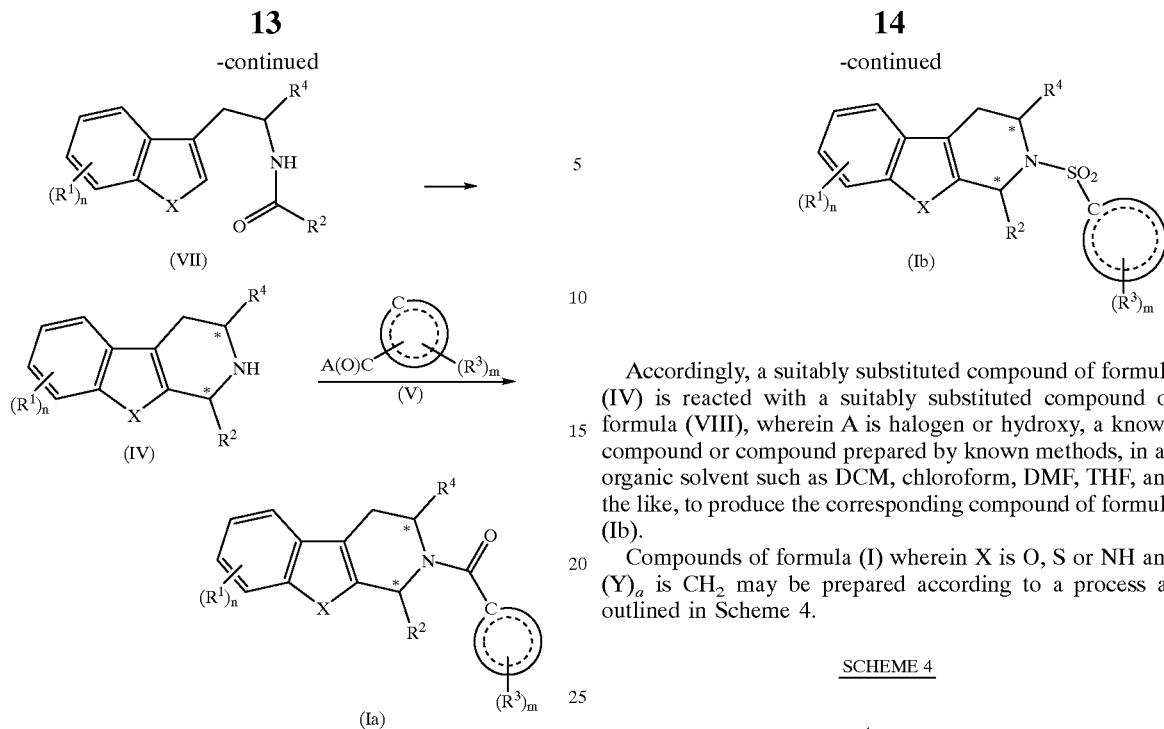

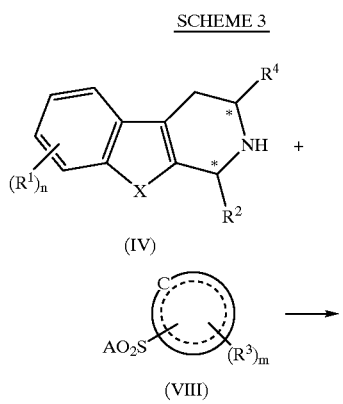

More particularly, a compound of formula (II), wherein X is O, S or NH, is reacted with a suitably substituted compound of formula (VI), wherein A is halogen or hydroxy, in an organic solvent such as DCM, THF, DMF, and the like, to produce the corresponding compound of formula (VII).

The compound of formula (VII) is cyclized by treatment with POCl₃, in an organic solvent such as toluene, benzene, and the like, followed by reduction with NaBH₄, in an organic solvent such as ethanol, isopropanol, and the like, to produce the corresponding compound of formula (IV).

The compound of formula (IV) is then reacted with a suitably substituted compound of formula (V) to produce the compound of formula (Ia) as outlined in Scheme 1.

Compounds of formula (I), wherein X is O, S or NH and (Y)$_a$ is SO$_2$ may be prepared according to a process as outlined in Scheme 3.

SCHEME 3

Accordingly, a suitably substituted compound of formula (IV) is reacted with a suitably substituted compound of formula (VIII), wherein A is halogen or hydroxy, a known compound or compound prepared by known methods, in an organic solvent such as DCM, chloroform, DMF, THF, and the like, to produce the corresponding compound of formula (Ib).

Compounds of formula (I) wherein X is O, S or NH and (Y)$_a$ is CH$_2$ may be prepared according to a process as outlined in Scheme 4.

SCHEME 4

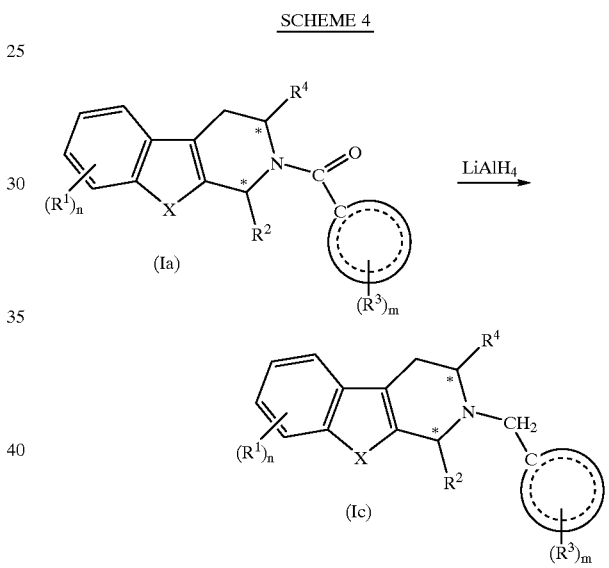

Accordingly, a suitably substituted compound of formula (Ia) is treated with a reducing agent such as LAH, diboron, and the like, preferably LAH, in an organic solvent such as methanol, THF, diethyl ether, and the like, preferably at a temperature in the range of about −20 to 40° C., to produce the corresponding compound of formula (Ic).

Compounds of formula (I) wherein (Y)$_a$ is CH$_2$ and X is NH, may alternatively be prepared according to a process as outlined in Scheme 5.

SCHEME 5

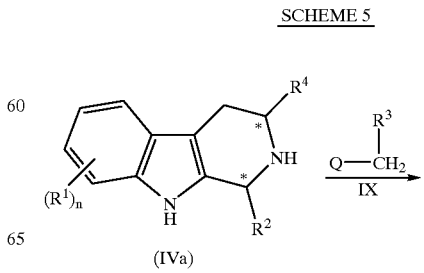

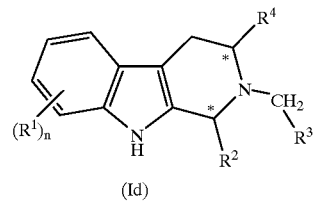

(Id)

Accordingly, a compound of formula (IVa) is reacted with a suitably substituted compound of formula (IX), wherein Q is halogen, O-tosylate or O-mesolate, in an organic solvent such as DCM, THF, and the like, to produce the corresponding compound of formula (Id).

Compounds of formula (I), wherein X is O, S or NH and $(Y)_a$ is $(Y)_0$ (i.e. wherein a is 0, such that Y is absent), may be prepared according to a process as outlined in Scheme 6.

SCHEME 6

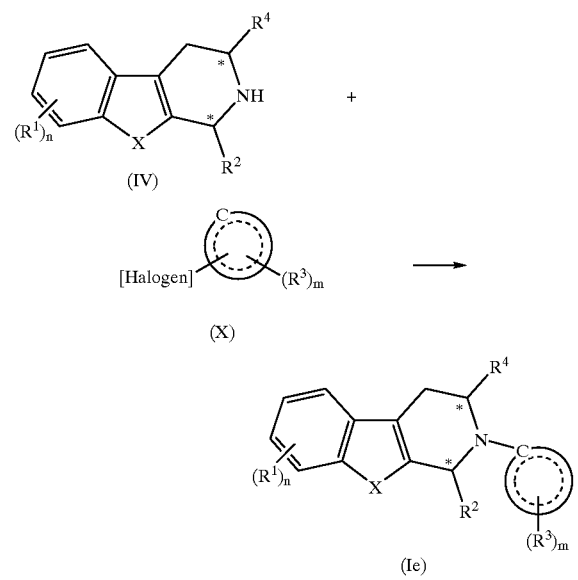

More specifically, a compound of formula (IV), a known compound or compound produced by known methods, is reacted with a suitably substituted halide of formula (X), a known compound or compound prepared by known methods, in an organic solvent such as toluene, DMF, 1-methyl-2-pyrrolidinone, and the like, preferably at a temperature in the range of about 80 to 250° C., to produce the corresponding compound of formula (Ie).

Compounds of formula (I) wherein X is $NR^D$ may be prepared by according to a process as outlined in Scheme 7.

SCHEME 7

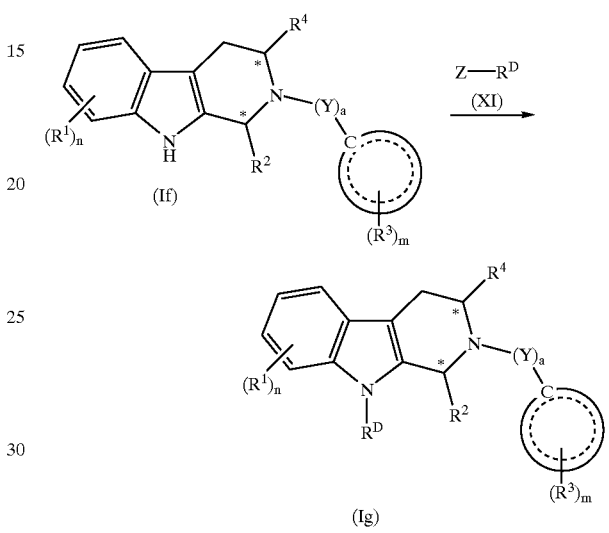

Accordingly, a compound of formula (If) is reacted with a compound of formula (XI), wherein Z is halogen, hydroxy, O-toylate or O-mesolate and a base such as sodium hydride, potassium t-butoxide, and the like, in a solvent such DMF, 1-methyl-2-pyrrolidinone, and the like, to produce the corresponding compound of formula (Ig).

Compounds of formula (I) wherein Z is CH—OH or C(O) may be prepared according to a process as outlined in Scheme 8.

SCHEME 8

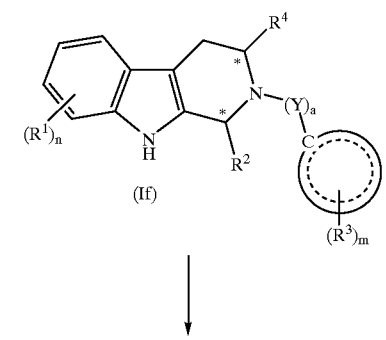

(If)

↓

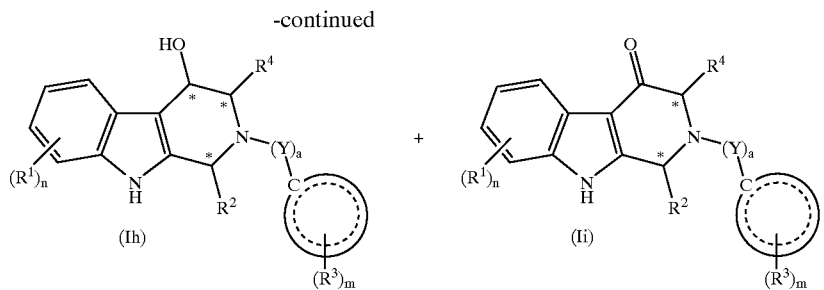

More particularly, a compound of formula (If) is treated with an oxidizing agent such as DDQ, chloranil, and the like, in a solvent such as THF, methanol, water, and the like, preferably at a temperature in the range of about −78 to about 30° C., to produce a mixture of the corresponding compounds of formula (Ih) and (Ii). Preferably, the compounds of formula (Ih) and (Ii) are separated by known methods, such as recrystallization, column chromatography, and the like.

Compounds of formula (I) wherein

is 2-thiazolyl, may be prepared according to a process as outlined in Scheme 9.

SCHEME 9

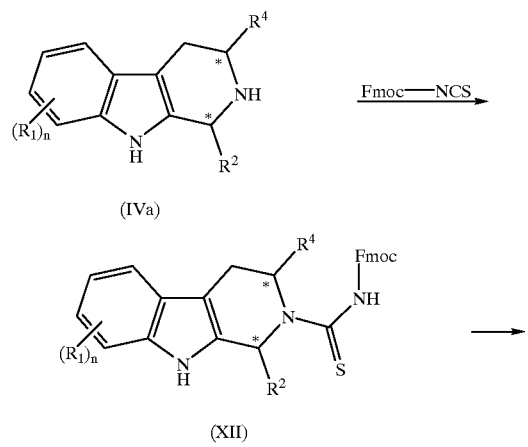

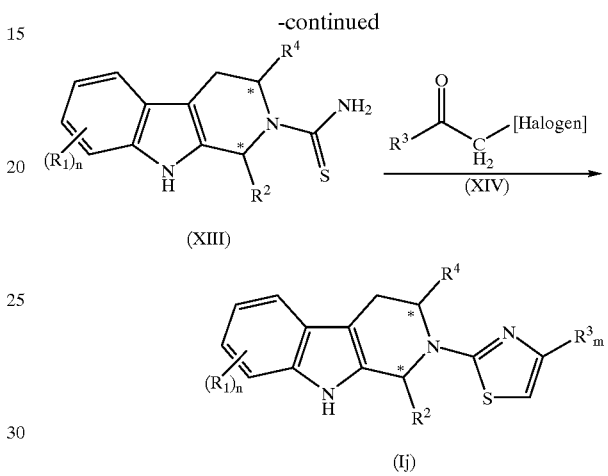

Accordingly, a suitably substituted compound of formula (IVa) is reacted with Fmoc-NCS, in an organic solvent such as DCM, DMF, THF, and the like, preferably at room temperature, to produce the corresponding compound of formula (XII).

The compound of (XII) is reacted with 20% piperidine, in an alcohol such as methanol, ethanol, and the like, to produce the corresponding amine of formula (XIII).

The amine of formula (XIII) is reacted with a suitably substituted α-halo methyl ketone of formula (XIV), in the presence of an organic solvent or mixture such as DMF, ethanol:dioxane, and the like, in the presence of a base such as TEA, DIPEA, and the like, preferably at a temperature of about 70° C., to produce the corresponding compound of formula (Ij).

Compounds of formula (I) wherein $(Y)_a$ is C(O)O, may be prepared according to the process outlined in Scheme 10.

SCHEME 10

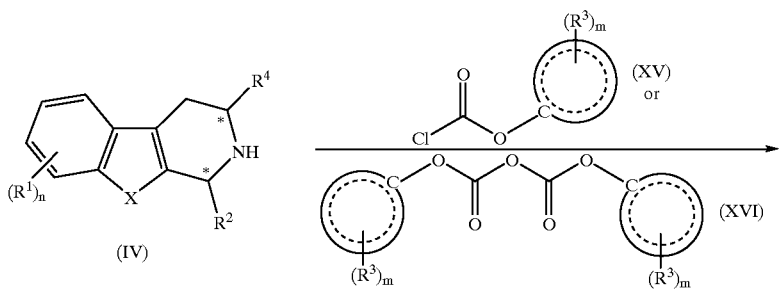

More particularly, a compound of formula (IV) is reacted with a suitably substituted chloroformate of formula (XV) or an anhydride of formula (XVI) in an organic solvent such as DCM, DMF, THF, and the like, to produce the corresponding compound of formula (Ik).

Compounds of formula (I) wherein $(Y)_a$ is C(O)—NH may be prepared according to a process as outlined in Scheme 11.

SCHEME 11

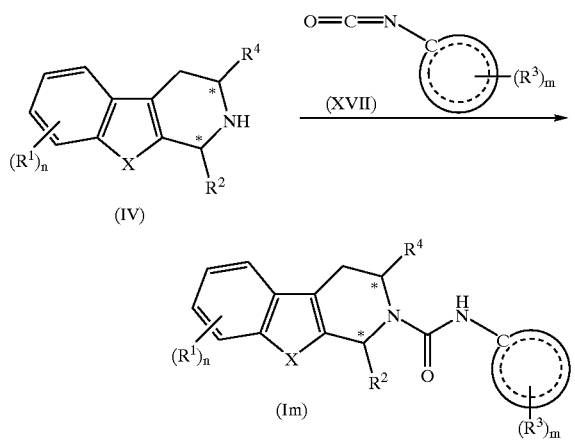

Accordingly, a compound of formula (IV) is reacted with a suitably substituted compound of formula (XVII), in an organic solvent such as DCM, DMF, THF, and the like, to produce the corresponding compound of formula (Im).

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis,* John Wiley & Sons, 1991. The protecting groups may be removed at a convenient subsequent stage using methods known from the art.

The utility of the compounds to treat sexual dysfunction can be determined according to the procedures described in Example 10, 11 and 12 herein.

The present invention therefore provides a method of treating sexual dysfunction in a subject in need thereof, which comprises administering any of the compounds as defined herein in a quantity effective to treat sexual dysfunction. The compound may be administered to a patient by any conventional route of administration, including, but not limited to, intravenous, oral, subcutaneous, intramuscular, intradermal and parenteral. The quantity of the compound which is effective for treating sexual dysfunction is between 0.1 mg per kg and 20 mg per kg of subject body weight.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 1 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

The method of treating sexual dysfunction, particularly male erectile dysfunction (ED) described in the present invention may also be carried out using a pharmaceutical composition comprising any of the compounds as defined herein and a pharmaceutically acceptable carrier. The pharmaceutical composition may contain between about 1 mg and 1000 mg, preferably about 10 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of sexual dysfunction, particularly male erectile dysfunction (ED) is required.

The daily dosage of the products may be varied over a wide range from 1 to 1,000 mg per adult human per day. For oral administration, the compositions are preferably provided in the form of tablets containing, 5.0, 10.0, 15.0, 25.0, 50.0, 100, 250 and 500 milligrams of the active ingredient for the symptomatic adjustment of the dosage to the patient to be treated. An effective amount of the drug is ordinarily supplied at a dosage level of from about 0.1 mg/kg to about 20 mg/kg of body weight per day. Preferably, the range is from about 0.2 mg/kg to about 10 mg/kg of body weight per day, and especially from about 0.5 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

Unless otherwise indicated, $^1$H NMRs were run on a Bruker AC-300.

EXAMPLE 1

1-(3,4-Methylenedioxyphenyl)-2-[5-(3-trifluoromethylphenyl)furoyl]-2,3,4,9-tetrahydro-1H-β-carboline (#58)

To a suspension of 5-(3-trifluoromethylphenyl)furoic acid (256 mg, 1 mmol) in DCM (20 mL, anhydrous) was added oxalyl chloride (165 mg, 1.3 mmol), followed by two drops of DMF. The mixture was stirred at room temperature for 1 h. A solution of 1-(3,4-methylenedioxyphenyl)-2,3,4,9-tetrahydro-1H-β-carboline (292 mg, 1 mmol) (prepared according to the process as disclosed in WO 97/43287, Intermediate 7, page 24) and triethylamine (0.4 mL) in DCM (10 mL, anhydrous) was added and the mixture was stirred at room temperature for 16 h, washed sequentially with aqueous NaHCO$_3$, brine (2X), 1N HCl and brine (2X) and dried with MgSO$_4$. After evaporation of the solvent, a white solid was obtained.

mp: 126–129° C.

MS (m/z): 531 (MH$^+$);

$^1$H-NMR (CDCl$_3$) δ2.96 (d, J=8 Hz, 1 H), 3.24 (m, 1 H), 3.56 (m, 1 H), 4.60 (d, J=8 Hz, 1 H), 5.90 (s, 2 H), 6.70 (d, J=8 Hz, 1 H), 6.83-6.99 (m, 4 H), 7.13-7.34 (m, 4 H), 7.55 (m, 3 H), 7.87 (d, J=7 Hz, 1 H), 7.95 (s, 1 H), 8.23 (s, 1 H);

EXAMPLE 2

9-[2-(Pyrrolidin-1-yl)-ethyl]-1-(3,4-methylenedioxyphenyl)-2-[5-(3-trifluoromethylphenyl)furoyl]-2,3,4-trihydro-1H-β-carboline (#75)

To a solution of 1-(3,4-methylenedioxyphenyl)-2-[5-(3-trifluoromethyl phenyl)furoyl]-2,3,4,9-tetrahydro-1H-β-carboline (prepared as in Example 1) (600 mg, 1.14 mmol) in DMF (15 mL, anhydrous) was added sodium hydride (60%, 105 mg, 2.6 mmol) at room temperature. The mixture was stirred at room temperature for 30 min. N-chloroethylpyrrolidine hydrochloride (214 mg, 1.26 mmol) and 15-crown ether-5 (1 drop) were added. The mixture was stirred at room temperature for 16 h, quenched with NH$_4$Cl, extracted with ethyl acetate and dried with MgSO$_4$. After evaporation of the solvent, the residue was purified by column chromatography (silica gel, ethyl acetate:hexanes=3:1) to yield a white solid.

MS (m/z): 628 (MH$^+$)

$^1$H-NMR (CDCl$_3$) δ1.26 (m, 4 H), 2.64 (m, 4 H), 2.89 (m, 2H), 3.05 (d, J=8 Hz, 1 H), 3.28 (t, J=8 Hz, 1 H), 3.59 (t, J=8 Hz, 1H), 3.96 (m, 1 H), 4.16 (m, 1 H), 4.58 (d, J=8 Hz, 1 H), 5.96 (s, 2 H), 6.75 (d, J=8 Hz, 1 H), 6.84 (m, 2 H), 7.02 (d, J=8 Hz, 1 H), 7.15-7.29 (m, 4 H), 7.43 (s, 1 H), 7.59 (m, 3 H), 7.89 (d, J=7 Hz, 1 H), 7.96 (s, 1 H)

The corresponding methanesulfonic acid salt was prepared by addition of 1.0 equivalent of methanesulfonic acid to a solution of the title compound in DCM to produce product for biological testing.

mp: 122–124° C.

EXAMPLE 3

1-(3,4-Methylenedioxyphenyl)-2-[5-(3,4-dimethoxyphenyl)pyrimidin-2-yl]-2,3,4,9-tetrahydro-1H-β-carboline (#7)

A solution of 1-(3,4-methylenedioxyphenyl)-2,3,4,9-tetrahydro-1H-β-carboline (3.73 g, 12.8 mmol) (prepared according to the process as disclosed in WO97/43287, Intermediate 7, page 24) and 2-chloro-5-(3,4-dimethoxyphenyl)pyrimidine (1.6 g, 6.4 mmol) in DMF (50 mL, anhydrous) was heated at 120° C. under stirring for 16 h. The reaction mixture was quenched with NH$_4$Cl and extracted with ethyl acetate. The organic phase was washed with brine (2×) and dried with MgSO$_4$. Column chromatography (silica gel, ethyl acetate:hexanes=2:3) yielded a white solid.

mp: 173–175° C.

MS (m/z): 507 (MH$^+$)

$^1$H-NMR (CDCl$_3$) δ2.91 (d, J=9 Hz, 1 H), 3.02 (td, J=9, 1 Hz, 1 H), 3.39 (td, J=9, 1 Hz, 1 H), 3.92 (s, 3 H), 3.94 (s, 3 H), 5.02 (d, J=9, 1 Hz, 1 H), 5.92 (s, 2 H), 6.72 (d, J=8 Hz, 1 H), 6.87-7.03 (m, 4 H), 7.11-7.17 (m, 3 H), 7.31 (d, J=8 Hz, 1 H), 7.56 (d, J=8 Hz, 1 H), 7.80 (s, 1 H), 8.56 (s, 2 H)

EXAMPLE 4

1-(3,4-Methylenedioxyphenyl)-2-[5-(3,4-dimethoxyphenyl)pyrimidin-2-yl]-9-dimethylaminoethyl-2,3,4-trihydro-1H-β-carboline (#5)

Following the procedure outlined in Example 2, 1-(3,4-methylenedioxyphenyl)-2-[5-(3,4-dimethoxyphenyl)pyrimidin-2-yl]-2,3,4,9-tetrahydro-1H-β-carboline (prepared as in Example 3) (1.0 g, 1.97 mmol), 2-chloro-N,N-dimethylethylamine hydrochloride (0.342 g, 2.37 mmol), sodium hydride (60%, 0.190 g, 4.74 mmol) and 15-crown ether-5 were reacted to yield the product as a slightly yellow solid (after column chromatography with silica gel, ethyl acetate).

MS (m/z): 578 (MH$^+$)

$^1$H-NMR (CDCl$_3$) δ2.21 (s, 6 H), 2.22 (m, 1 H), 2.61 (m, 1 H), 2.89 (dd, J=13, 4 Hz, 1 H), 3.03 (td, J=13, 4 Hz, 1 H), 3.35 (td, J=13, 4 Hz, 1 H), 3.91 (m, 1 H), 3.92 (s, 3 H), 3.95 (s, 3 H), 4.06 (m, 1 H), 4.96 (dd, J=13, 4 Hz, 1H), 5.93 (s, 2 H), 6.72 (d, J=8 Hz, 1 H), 6.83 (d, 1 H), 6.85-6.98 (m, 4H), 7.12 (d, J=8 Hz, 1 H), 7.21 (d, J=8 Hz, 1 H), 7.31 (d, J=8 Hz, 1 H), 7.34 (s, 1 H), 7.58 (d, J=8 Hz, 1 H), 8.56 (s, 2 H)

EXAMPLE 5

1-(3,4-Methylenedioxyphenyl)-2-[5-(4-methoxyphenyl)-pyrimidin-2-yl-]-4-oxo-2,3,4,9-tetrahydro-1H-β-carboline (#157) &

1-(3,4-Methylenedioxy-phenyl)-2-[5-(4-methoxyphenyl)-pyrimidin-2-yl-]-4-hydoxy-2,3,4,9-tetrahydro-1H-β-carboline (#158)

To a mixture of DDQ (113.5 mg, 0.5 mmol) and 1-(3,4-methylenedioxyphenyl)-2-[5-(3,4-dimethoxyphenyl)pyrimidin-2-yl]-2,3,4,9-tetrahydro-1H-β-carboline (prepared as in Example 3) (51 mg, 0.1 mmol) was added a mixed solvent of THF:water (9:1) at −78° C. The mixture was stirred at 0° C. and allowed to warm to room temperature over a period of 15 h. Column chromatography (silica gel, hexanes:ethyl acetate=1:1) yielded the-oxo- and -hydroxy derivatives respectively, as white solids.

157:

MS (m/z) 521 (MH$^+$), 519 (M-1)

$^1$H NMR (CDCl$_3$) δ3.90 (d, J=18 Hz, 1H), 3.89 (s, 3H), 3.91 (s, 3H), 5.43 (d, J=18 Hz, 1 H), 5.84 (s, 2 H), 6.62 (d, J=8 Hz, 1 H), 6.71 (d, J=8 Hz, 1 H), 6.88-7.00 (m, 4 H), 7.29-7.43 (m, 3 H), 7.53 (s, 1 H), 8.25 (m, 1H), 8.51 (s, 2 H); 9.55 (s, 1 H)

158:

MS (m/z) 523 (MH$^+$), 521 (M-1)

$^1$H NMR (CDCl$_3$) δ3.30 (t, J=6 Hz, 1 H), 3.69 (d, J=6 Hz, 1 H), 3.92 (s, 3 H), 3.94 (s, 3 H), 5.97 (s, 2H), 6.11 (s, 1H), 6.71 (d, J=8 Hz, 1H), 6.93-7.05 (m, 4 H), 7.18 (d, J=8 Hz, 1H), 7.23 (d, J=8 Hz, 1H), 7.40 (t, J=6 Hz, 1H), 7.49 (d, J=8 Hz, 1 H), 7.82 (d, J=8 Hz, 1 H), 8.43 (s, 2 H); 9.15 (s, 1 H)

EXAMPLE 6

1-(3,4-Methylenedioxphenyl)-2-[4-(4-methoxyphenyl)thiazol-2-yl]-2,3,4,9-tetrahydro-1H-β-carboline (#169)

A. 1-(3,4-Methylenedioxyphenyl)-2-[3-(fluorenylmethyloxycarbonyl)thiocarbamoyl]-2,3,4,9-tetrahydro-1H-β-carboline A mixture of 1-(3,4-methylenedioxyphenyl)-2,3,4,9-tetrahydro-1H-β-carboline (2.66 g, 9.08 mmol) (prepared according to the process as disclosed in WO97/43287, Intermediate 7, page 24) and Fmoc-isothiocyanate (2.82 g, 10.14 mmol) was dissolved in dry dichloromethane (50 mL). The mixture was stirred for 16 hours at ambient temperature, and then concentrated in vacuo. Purification by flash chromatography (0–10% methanol in dichloromethane) yielded the protected thiourea as a pale yellow solid.

MS (m/z): 574 (MH$^+$)

$^1$H-NMR (CDCl$_3$) δ2.86 (dd, J=12.9, 5.1 Hz, 1 H), 3.09 (dt, J=17.1, 6.9 Hz, 1 H), 3.56 (dt, J=12.9, 5.1 Hz, 1 H), 4.19 (t, J=6.9 Hz, 1H), 4.43-4.53 (m, 2 H), 5.91 (s, 2 H), 6.70 (d, J=8 Hz, 1 H), 6.90 (br d, J=7.6 Hz, 1 H), 6.97 (br s, 1 H), 7.11-7.78 (series of m, 17 H)

B. 1-(3,4-Methylenedioxyphenyl)-2-(thiocarbamoyl)-2,3,4,9-tetrahydro-1H-β-carboline A solution of the protected thiourea from Part A (4.78 g, 8.33 mmol) in 20% (v/v) piperidine in methanol was heated to reflux for 5 h. The mixture was concentrated in vacuo to yield a crude residue which was purified by flash chromatography (SiO$_2$, 0–10% methanol in dichloromethane) to yield a yellow solid.

MS (m/z): 352 (MH$^+$)

$^1$H-NMR (CDCl$_3$) δ2.69-2.87 (series of m, 2 H), 3.10-3.19 (m, 1 H), 4.24 (br s,1 H), 6.00 (d, J=3.3 Hz, 2 H), 6.72 (d, J=8.0 Hz, 1 H), 6.87 (d, J=8.0 Hz, 1 H), 7.00-7.11 (series of m, 3 H), 7.30 (d, J=8.0 Hz, 1H), 7.46 (d, J=7.7 Hz, 1H), 7.74 (br s, 3 H), 11.06 (s, 1 H)

C. 1-(3,4-Methylenedioxyphenyl)-2-[4-(4-methoxyphenyl)thiazol-2yl]-2,3,4,9-tetrahydro-1H-β-carboline (#169)

To a solution of the thiourea from Part B (223 mg, 0.63 mmol) in a 1:1 mixture of dioxane:ethanol (5 mL) was added 4-methoxyphenyl-2'-bromoacetophenone (175 mg, 0.76 mmol) and triethylamine (0.40 mL). The mixture was heated to 70° C. for 3 h, cooled to room temperature and concentrated in a rotary evaporator. The residue was purified by flash chromatography (SiO$_2$, 0–10% methanol in dichloromethane) to yield a colorless solid.

MS (m/z): 482 (MH$^+$)

$^1$H-NMR (CDCl$_3$) δ2.86-2-3.07 (series of m, 2 H), 3.61-3.71 (m, 1 H), 3.78 (s, 3 H), 3.91-4.02 (m, 1 H), 5.99 (d, J=3.3 Hz, 2H), 6.58 (s, 1H), 6.80-7.11 (series of m, 8 H), 7.31 (d, J=7.8 Hz, 1 H), 7.48 (d, J=7.6 Hz, 1 H), 7.82 (d, J=8.7 Hz, 2 H), 10.93 (s, 1 H)

EXAMPLE 7

1-(3,4-Methylenedioxyiphenyl)-2-[4-phenylthiazol-2-yl]-2,3,4,9-tetrahydro-1H-β-carboline (#170)

A. 1-(3,4-Methylenedioxyphenyl)-2-[3-(fluorenylmethyloxycarbonyl)thiocarbamoyl]-2,3,4,9-tetrahydro-1H-β-carboline A mixture of 1-(3,4-methylenedioxyphenyl)-2,3,4,9-tetrahydro-1H-β-carboline (2.66 g, 9.08 mmol) (prepared according to the process as disclosed in WO97/43287, Intermediate 7, page 24) and Fmoc-isothiocyanate (2.82 g, 10.14 mmol) was dissolved in dry dichloromethane (50 mL). The mixture was stirred for 16 hours at ambient temperature, and then concentrated in vacuo. Purification by flash chromatography (0–10% methanol in dichloromethane) yielded the protected thiourea as a pale yellow solid.

MS (m/z): 574 (MH$^+$)

$^1$H-NMR (CDCl$_3$) δ2.86 (dd, J=12.9, 5.1 Hz, 1 H), 3.09 (dt, J=17.1, 6.9 Hz, 1 H), 3.56 (dt, J=12.9, 5.1 Hz, 1 H), 4.19 (t, J=6.9 Hz, 1H), 4.43-4.53 (m, 2 H), 5.91 (s, 2 H), 6.70 (d, J=8 Hz, 1 H), 6.90 (br d, J=7.6 Hz, 1H), 6.97 (br s, 1H), 7.11-7.78 (series of m, 17 H)

B. 1-(3,4-Methylenedioxyphenyl)-2-(thiocarbamoyl)-2,3,4,9-tetrahydro-1H-β-carboline A solution of the protected thiourea from Part A (4.78 g, 8.33 mmol) in 20% (v/v) piperidine in methanol was heated to reflux for 5 h. The mixture was concentrated in vacuo to yield a crude residue which was purified by flash chromatography (SiO$_2$, 0–10% methanol in dichloromethane) to yield a yellow solid.

MS (m/z): 352 (MH$^+$)

$^1$H-NMR (CDCl$_3$) δ2.69-2.87 (series of m, 2 H), 3.10-3.19 (m, 1 H), 4.24 (br s, 1 H), 6.00 (d, J=3.3 Hz, 2 H), 6.72 (d, J=8.0 Hz, 1H), 6.87 (d, J=8.0 Hz, 1 H), 7.00-7.11 (series of m, 3 H), 7.30 (d, J=8.0 Hz, 1H), 7.46 (d, J=7.7 Hz, 1H), 7.74 (br s, 3 H), 11.06 (s, 1 H)

C. 1-(3,4-Methylenedioxyphenyl)-2-[4-phenylthiazol-2yl]-2,3,4,9-tetrahydro-1H-β-carboline (#170)

To a solution of the thiourea of Part B (227 mg, 0.65 mmol) was added β-bromoacetophenone (159 mg, 0.80 mmol) and triethylamine (0.40 mL). This mixture was heated to 70° C. for 3 h, cooled to room temperature and concentrated in a rotary evaporator. The residue was purified by flash chromatography (SiO$_2$, 0–10% methanol in dichloromethane) to yield a pale yellow solid.

MS (m/z): 452 (MH$^+$)

$^1$H-NMR (CDCl$_3$) δ2.87-2-3.06 (series of m, 2 H), 3.63-3.73 (m, 1 H), 3.93-3.99 (m, 1 H), 5.99 (d, J=3.3 Hz, 2 H), 6.59 (s, 1 H), 6.81-7.11 (series of m, 5 H), 7.25-7.69 (series of m, 6 H), 7.89 (d, J=7.4 Hz, 2 H), 10.95 (s, 1 H)

EXAMPLE 8

1-(2,3-Dihydro-benzofuran-5-yl)-2-[5-(2,3-dimethyl-3H-imidazol-4-yl)-pyrimidin-2-yl]-2,3,4,9-tetrahydro-1H-β-carboline (#190)

2-(5-bromo-2-pyrimidinyl)-1-(2,3-dihydro-5-benzofuranyl)-2,3,4,9-tetrahydro-1H-β-carboline (0.45 g, 1.00 mmol), 1,2-dimethyl-1H-imidazole (0.18 g, 1.87 mmol), Pd(OAc)$_2$ (12 mg, 0.05 mmol), PPh$_3$ (26 mg, 0.1 mmol) and K$_2$CO$_3$ (0.28 g, 2 mmol) were stirred in 3.5 mL DMF at 140° C. for 14 hours. The mixture was poured into aqueous 10% NaOH solution (50 mL). The resulting solution was extracted with CH$_2$Cl$_2$ (3×50 mL) and dried over Na$_2$SO$_4$. Purification by preparative TLC yielded the title product as yellow powder.

$^1$H NMR 300 MHz (CDCl$_3$) δ2.21 (s, 3H), 2.35 (s, 3H), 2.90 (m, 2H), 3.10 (t, 2H, J=8.8. Hz), 3.35 (m, 1H), 4.52 (t, 2H, J=8.8. Hz), 4.91 (m, 1H), 6.68~7.61 (m, 10 H)

MS (m/z) 463 (MH$^+$), 461 (MH$^-$).

EXAMPLE 9

2-[2,3']Bipyridinyl-6'-yl-1-(2,3-dihydro-benzofuran-5-yl)-2,3,4,9-tetrahydro-1H-β-carboline (#191)

A: 2-(5-Bromo-pyridin-2-yl)-1-(2,3-dihydro-benzofuran-5-yl)-2,3,4,9-tetrahydro-1H-β-carboline 1-(2,3-dihydro-5-benzofuranyl)-2,3,4,9-tetrahydro-1H-β-carboline (11.6 g, 40 mmol), 2,5-dibromopyridine (10.42 g, 44 mmol), Pd$_2$dba$_3$ (1.465 g, 1.6 mmol), dppp (1.32 g, 3.2 mmol) and NaOtBu (5.38 g, 56 mmol) were stirred in 60 mL DMF at 80° C. for 3 days. The reaction mixture was filtered through a plug of Celite with CH$_2$Cl$_2$. The reaction mixture was then concentrated, the crude mixture was then loaded on Foxy column (110 g silica gel) and eluted with ethyl acetate/hexane (3:7). The product crystallized out in test tubes. The product was concentrated and then recrystallized from THF to yield the product as yellow crystals.

$^1$H NMR 400 MHz (THF-d8) δ0.91 (m, 1H), 1.15 (m, 1H), 1.25(t, 2H, J=9.5 Hz), 1.60 (m, 1H), 2.31 (m, 1H), 2.60

(t, 2H, J=9.5 Hz), 4.75 (d, 1H, J=7.6 H), 5.02 (d, 1H, J=7.6 Hz), 5.10~5.28 (m, 4H), 5.380 (m, 2H), 5.58 (m, 1H), 5.72 (m, 1H), 6.28 (s, 1H), 8.12 (s, 1H)

MS (m/z) 446, 448 (MH$^+$), 444,446 (MH$^-$).

B: 2-[2,3']Bipyridinyl-6'-yl-1-(2,3-dihydro-benzofuran-5-yl)-2,3,4,9-tetrahydro-1H-β-carboline The product from step A above, (0.4 g, 0.896 mmol), 2-tributylstannanylpyridine (0.8 g, 2.17 mmol) and Pd(PPh$_3$)$_4$ (0.12 g, 0.104 mmol) were stirred in 1,4-dioxane (5 mL) at 88° C. for 24 h. The reaction mixture was filtered through a plug of Celite with CH$_2$Cl$_2$ and then concentrated to a small volume. Preparative TLC (3:7 ethyl acetate/hexane; then 5% CH$_3$OH/CH$_2$Cl$_2$) yielded the product as a yellow solid.

$^1$H NMR (CDCl$_3$) δ2.82 (m, 1H), 3.10 (m, 3H), 3.58 (m, 1H), 4.31 (m, 1H), 4.53 (t, 2H, J=9.5 z), 6.71 (,d, 1H, J=7.6 Hz), 6.85 (d, 1H, J=7.6 Hz)

MS (m/z) 445, (MH$^+$), 443 (MH$^-$)

Following procedures as described herein, the compounds as listed in Tables 1–6 were prepared.

TABLE 1

| Cmpd # | R$^D$ | R$^2$ | C | R$^3$ |
|---|---|---|---|---|
| 1 | H | 3,4-methylene dioxyphenyl | — | — |
| 2 | dimethyl aminoethyl | 3,4-methylene dioxyphenyl | 2-benzothiazolyl | — |
| 3 | H | 3,4-methylene dioxyphenyl | 2-benzothiazolyl | — |
| 4 | dimethyl aminoethyl | 3,4-methylene dioxyphenyl | 2-pyrimidinyl | 5-(4-chlorophenyl) |
| 5 | dimethyl aminoethyl | 3,4-methylene dioxyphenyl | 2-pyrimidinyl | 5-(3,4-di methoxyphenyl) |
| 6 | dimethyl aminoethyl | 3,4-methylene dioxyphenyl | 2-pyrimidinyl | 5-(4-methoxy phenyl) |
| 7 | H | 3,4-methylene dioxyphenyl | 2-pyrimidinyl | 5-(3,4-dimethoxy phenyl) |
| 8 | H | 3,4-methylene dioxyphenyl | 2-pyrimidinyl | 5-(2-nitro-4-methylsulfonyl) phenyl |
| 9 | H | 3,4-methylene dioxyphenyl | 2-pyrimidinyl | 5-(4-methoxy phenyl) |
| 10 | H | 3,4-methylene dioxyphenyl | 2-pyrimidinyl | 5-(4-chloro phenyl) |
| 148 | 2-(N-pyrrolidinyl) ethyl | 3,4-methylene dioxyphenyl | 2-pyrimidinyl | 5-(4-methoxy phenyl) |
| 150 | 2-benzoxazolyl | 3,4-methylene dioxyphenyl | 2-benzoxazolyl | — |
| 151 | H | 3,4-methylene dioxyphenyl | 2-benzoxazolyl | — |
| 153 | H | 3,4-methylene dioxyphenyl | 2-pyrimidinyl | 5-(2-pyridyl) |
| 154 | 2-(N-pyrrolidinyl) ethyl | 3,4-methylene dioxyphenyi | 2-pyrimidinyl | 5-(2-nitro-4-methylsulfonyl phenyl) |
| 155 | dimethyl aminoethyl | 3,4-methylene dioxyphenyl | 2-benzoxazolyl | — |
| 156 | dimethyl aminoethyl | 3,4-methylene dioxyphenyl | 2-pyrimidinyl | 5-(2-pyridyl) |
| 161 | H | 3,4-methylene dioxyphenyl | 2-pyrimidinyl | 5-(4-methyl phenyl) |
| 166 | 5-(4-methyl phenyl)-2-pyrimidinyl | 3,4-methylene dioxyphenyl | 2-pyrimidinyl | 5-(4-methyl phenyl) |
| 167 | H | 3,4-dimethoxy phenyl | 2-pyrimidinyl | 5-(3,4-dimethoxy phenyl) |
| 168 | H | 3,4-methylene dioxyphenyl | 2-pyrimidinyl | — |
| 169 | H | 3,4-methylene dioxyphenyl | 2-thiazolyl | 4-(4-methoxy phenyl) |
| 170 | H | 3,4-methylene dioxyphenyl | 2-thiazolyl | 4-phenyl |
| 172 | H | 3,4-methylene dioxyphenyl | 2-benz imidazolyl | — |

TABLE 1-continued

| Cmpd # | R^D | R² | (C ring) | R³ |
|---|---|---|---|---|
| 173 | H | 3,4-methylene dioxyphenyl | 2-pyrimidinyl | — |
| 174 | H | 5-(2,3-dihydro)-benzofuryl | 2-pyrimidinyl | 5-(4-methoxy phenyl) |
| 175 | H | 3,4-methylene dioxyphenyl | 2-pyrimidinyl | 5-(3,4-dimethoxy phenyl) |
| 176 | H | R-3,4-methylene dioxyphenyl | 2-pyrimidinyl | 5-(3,4-dimethoxy phenyl) |
| 177 | H | 5-(2,3-dihydro)-benzofuryl | 2-pyrimidinyl | 5-(4-hydroxy phenyl) |
| 178 | H | 5-(2,3-dihydro)-benzofuryl | 2-pyrimidinyl | 5-(4-[2-(N-pyrrolidinyl)ethoxy]phenyl) |
| 179 | H | 3,4-methylene dioxyphenyl | 2-pyrimidinyl | 5-bromo |
| 180 | H | 5-(2,3-dihydro)-benzofuryl | 2-pyrimidinyl | 5-(4-(2-(4-morpholinyl)ethoxy)phenyl) |
| 181 | H | 5-(2,3-dihydro)-benzofuryl | 2-pyrimidinyl | 5-(4-(2-(dimethyl amino)ethoxy)phenyl) |
| 182 | H | 5-(2,3-dihydro)-benzofuryl | 2-pyrimidinyl | 5-(2-pyridyl) |
| 183 | H | 3,4-methylene dioxyphenyl | 2-pyrimidinyl | 5-(2-pyridyl) |
| 184 | H | 6-(2,3-dihydrobenzo-[1,4]-dioxin-6-yl) | 2-pyrimidinyl | 5-(4-methoxy phenyl) |
| 185 | H | 5-(2,3-dihydro)-benzofuryl | 2-pyrimidinyl | 5-(3-pyridyl) |
| 186 | H | 5-(2,3-dihydro)-benzofuryl | 2-pyrimidinyl | 5-bromo |
| 187 | H | 5-(2,3-dihydro)-benzofuryl | 2-pyrimidinyl | 5-(2-pyridyl) |
| 188 | H | 6-(2,3-dihydrobenzo-[1,4]-dioxin-6-yl) | 2-pyrimidinyl | 5-(4-methoxy phenyl) |
| 189 | H | 3,4-methylene dioxyphenyl | 2-pyrimidinyl | 5-(2-pyridyl) |
| 190 | H | 5-(2,3-dihydro benzofuryl) | 2-pyrimidinyl | 5-(2,3-dimethyl-3H-imidazol-4-yl) |
| 191 | H | 5-(2,3-dihydro benzofuryl) | 2-pyridyl | 5-(2-pyridyl) |

TABLE 2

| Cmpd # | R^D | R² | Y | 2-furyl etc. | R³ |
|---|---|---|---|---|---|
| 11 | H | 3,4-methylene dioxyphenyl | CH₂ | 2-furyl | 5-(2-chloro-5-trifluoromethyl phenyl) |
| 12 | H | 3,4-methylene dioxyphenyl | CH₂ | 2-furyl | 5-(3-trifluoro methylphenyl) |
| 13 | dimethyl aminoethyl | 3,4-methylene dioxyphenyl | C(O) | 2-benzo(b)furyl | 5-nitro |
| 14 | H | 3,4-methylene dioxyphenyl | C(O) | 2-benzo(b)furyl | 5-nitro |
| 15 | H | 3,4-methylene dioxyphenyl | C(O) | 2-benzo(b)furyl | 6-methoxy |
| 16 | H | 3,4-methylene dioxyphenyl | C(O) | 2-benzo(b)furyl | — |
| 17 | dimethyl aminoethyl | 3,4-methylene dioxyphenyl | C(O) | 2-benzo(b) thienyl | — |
| 18 | H | 4-methylene dioxyphenyl | C(O) | 2-benzo(b) thienyl | — |
| 19 | 2-(3-nitro phenyl)-5-furylcarbonyl | 3,4-(difluoro methylene dioxy)phenyl | C(O) | 2-furyl | 5-(3-nitro phenyl) |
| 20 | 2-(3-trifluoro methylphenyl)-5-furyl carbonyl | 3,4-(difluoro methylene dioxy)phenyl | C(O) | 2-furyl | 5-(3-trifluoro methylphenyl) |
| 21 | H | 3,4-(difluoro methylene dioxy)phenyl | C(O) | 2-furyl | 5-(3-nitro phenyl) |
| 22 | H | 3,4-(difluoro methylene dioxy)phenyl | C(O) | 2-furyl | 5-(3-trifluoro methylphenyl) |
| 23 | 2-methoxy carbonylethyl | 3,4-methylene dioxyphenyl | C(O) | 2-furyl | 5-(3-trifluoro methylphenyl) |
| 24 | 2-methoxy carbonyl methyl | 3,4-methylene dioxyphenyl | C(O) | 2-furyl | 5-(3-nitro phenyl) |
| 25 | 2-methoxy carbonyl methyl | 3,4-methylene dioxyphenyl | C(O) | 2-furyl | 5-(3-trifluoro methylphenyl) |
| 26 | 2-pyridyl methyl | 3,4-methylene dioxyphenyl | C(O) | 2-furyl | 5-(3-trifluoro methylphenyl) |
| 27 | 4-chloro-n-butyl | 3,4-methylene dioxyphenyl | C(O) | 2-furyl | 5-(3-trifluoro methylphenyl) |
| 28 | 4-morpholinyl ethyl | 3,4-methylene dioxyphenyl | C(O) | 2-furyl | 5-(3-trifluoro methylphenyl) |
| 29 | carboxyethyl | 3,4-methylene dioxyphenyl | C(O) | 2-furyl | 5-(3-trifluoro methylphenyl) |
| 30 | carboxy methyl | 3,4-methylene dioxyphenyl | C(O) | 2-furyl | 5-(3-nitro phenyl) |
| 31 | carboxy methyl | 3,4-methylene dioxyphenyl | C(O) | 2-furyl | 5-(3-trifluoro methylphenyl) |
| 33 | diethylamino ethyl | 3,4-methylene dioxyphenyl | C(O) | 2-furyl | 5-(3-trifluoro methylphenyl) |
| 34 | dimethyl aminobutyl | 3,4-methylene dioxyphenyl | C(O) | 2-furyl | 5-(3-trifluoro methylphenyl) |
| 35 | dimethyl aminoethyl | 3,4-methylene dioxyphenyl | C(O) | 2-furyl | 5-(3-trifluoro methylphenyl) |
| 36 | dimethyl aminoethyl | 3,4-methylene dioxyphenyl | C(O) | 2-furyl | 5-t-butyl |
| 37 | dimethyl aminoethyl | 3,4-methylene dioxyphenyl | C(O) | 2-furyl | 5-(4-nitro phenyl) |
| 38 | dimethyl aminoethyl | 3,4-methylene dioxyphenyl | C(O) | 2-furyl | 5-(3-nitro phenyl) |
| 39 | dimethyl | 3,4-methylene | C(O) | 2-furyl | 5-(4-chloro |

TABLE 2-continued

| Cmpd # | R^D | R^2 | Y | C | R^3 |
|---|---|---|---|---|---|
| 40 | dimethyl aminoethyl | 3,4-methylene dioxyphenyl | C(O) | 2-furyl | 5-(2-nitro-4-chlorophenyl) |
| 41 | dimethyl aminoethyl | 3,4-methylene dioxyphenyl | C(O) | 2-furyl | 5-(2-nitro phenyl) |
| 42 | dimethyl aminoethyl | 3,4-methylene dioxyphenyl | C(O) | 2-furyl | 5-(2-nitro-4-methylphenyl) |
| 43 | dimethyl aminoethyl | 3,4-methylene dioxyphenyl | C(O) | 2-furyl | 5-(2-chloro-5-trifluoromethyl phenyl) |
| 44 | dimethyl aminopropyl | 3,4-methylene dioxyphenyl | C(O) | 2-furyl | 5-(3-trifluoro methylphenyl) |
| 74 | 4-pyridyl methyl | 3,4-methylene dioxyphenyl | C(O) | 2-furyl | 5-(3-trifluoro methylphenyl) |
| 75 | pyrrolidinyl ethyl | 3,4-methylene dioxyphenyl | C(O) | 2-furyl | 5-(3-trifluoro methylphenyl) |
| 45 | H | 3,4-methylene dioxyphenyl | C(O) | 2-furyl | 5-(4-amino phenyl) |
| 46 | H | 3,4-methylene dioxyphenyl | C(O) | 2-furyl | 5-(4-chloro phenyl) |
| 47 | H | 3,4-methylene dioxyphenyl | C(O) | 2-furyl | 5-(2-nitro-4-chlorophenyl) |
| 48 | H | 3,4-methylene dioxyphenyl | C(O) | 2-furyl | 5-[4-(3-carboxy)-n-propylcarbonyl aminophenyl] |
| 49 | H | 3,4-methylene dioxyphenyl | C(O) | 2-furyl | 5-(4-acetyl aminophenyl) |
| 50 | H | 3,4-methylene dioxyphenyl | C(O) | 2-furyl | 5-(4-nitro phenyl) |
| 51 | H | 3,4-methylene dioxyphenyl | C(O) | 2-furyl | 5-(2-nitro-4-chloro phenyl) |
| 52 | H | 3,4-methylene dioxyphenyl | C(O) | 2-furyl | 5-[4-(3-carboxy)-n-propylcarbonyl aminophenyl] |
| 53 | H | 3,4-methylene dioxyphenyl | C(O) | 2-furyl | 5-(2-nitro-4-methylphenyl) |
| 54 | H | 3,4-methylene dioxyphenyl | C(O) | 2-furyl | 5-(3-nitro phenyl) |
| 55 | H | 3,4-methylene dioxyphenyl | C(O) | 2-furyl | 5-(3-acetyl aminophenyl) |
| 56 | H | 3,4-methylene dioxyphenyl | C(O) | 2-furyl | 5-(2-nitro phenyl) |
| 57 | H | 3,4-methylene dioxyphenyl | C(O) | 2-furyl | 5-(2-chloro-5-trifluoromethyl phenyl) |
| 58 | H | 3,4-methylene dioxyphenyl | C(O) | 2-furyl | 5-(3-trifluoro methylphenyl) |
| 59 | H | 3,4-methylene dioxyphenyl | C(O) | 2-furyl | 5-(3-amino phenyl) |
| 60 | H | 3,4-methylene dioxyphenyl | C(O) | 2-furyl | 5-[4-(4-hydroxy-n-butyl)amino phenyl] |
| 61 | H | 3,4-methylene dioxyphenyl | C(O) | 2-furyl | 5-[2-(dimethyl amino)methyl carbonylamino phenyl] |
| 62 | H | 3,4-methylene dioxyphenyl | C(O) | 2-furyl | 5-trifluoro methyl |
| 63 | H | 3,4-methylene dioxyphenyl | C(O) | 2-furyl | 5-bromo |
| 64 | H | 3,4-methylene dioxyphenyl | C(O) | 2-furyl | 5-nitro |

TABLE 2-continued

| Cmpd # | R^D | R^2 | Y | (ring) | R^3 |
|---|---|---|---|---|---|
| 65 | H | 3,4-methylene dioxyphenyl | C(O) | 2-furyl | 5-t-butyl |
| 66 | H | 3,4-methylene dioxyphenyl | C(O) | 2-furyl | 5-(2-nitro-4-chlorophenyl) |
| 78 | H | 3-pyridyl | C(O) | 2-furyl | 5-(3-trifluoro methylphenyl) |
| 79 | H | 4-chlorophenyl | C(O) | 2-furyl | 5-(3-trifluoro methylphenyl) |
| 80 | H | 4-cyanophenyl | C(O) | 2-furyl | 5-(3-nitro phenyl) |
| 81 | H | 4-cyanophenyl | C(O) | 2-furyl | 5-(3-trifluoro methylphenyl) |
| 82 | H | 4-dimethyl aminophenyl | C(O) | 2-furyl | 5-(3-trifluoro methylphenyl) |
| 83 | H | 4-dimethyl aminophenyl | C(O) | 2-furyl | 5-(3-nitro phenyl) |
| 84 | H | 4-nitrophenyl | C(O) | 2-furyl | 5-(3-trifluoro methylphenyl) |
| 85 | H | 4-nitrophenyl | C(O) | 2-furyl | 5-(3-nitro phenyl) |
| 86 | H | 4-pyridyl | C(O) | 2-furyl | 5-(3-nitro phenyl) |
| 87 | H | 4-pyridyl | C(O) | 2-furyl | 5-(3-trifluoro methylphenyl) |
| 88 | H | phenyl | C(O) | 2-furyl | 5-(3-trifluoro methylphenyl) |
| 89 | H | 3,4-methylene dioxyphenyl | C(O) | 2-thiazolyl | 4-methyl-5-(4-trifluoro methylphenyl) |
| 90 | H | 3,4-methylene dioxyphenyl | C(O) | 2-thienyl | 4-phenyl-5-trifluoromethyl |
| 91 | H | 3,4-methylene dioxyphenyl | C(O) | 2-thienyl | 5-(4-chloro phenyl) |
| 92 | H | 3,4-dimethyl phenyl | C(O) | 3-(1,2,5-triazolyl) | 1-phenyl-4-methyl |
| 93 | H | 3,4-dichloro phenyl | C(O) | 3-(1,2,5-triazolyl) | 1-phenyl-4-methyl |
| 94 | H | 3,4-dimethoxy phenyl | C(O) | 3-(1,2,5-triazolyl) | 1-phenyl-4-methyl |
| 95 | H | 3,4-dimethyl phenyl | C(O) | 3-(1,2,5-triazolyl) | 1-phenyl-4-methyl |
| 96 | H | 3,4-methylene dioxyphenyl | C(O) | 3-(1,2,5-triazolyl) | 1-phenyl-4-methyl |
| 97 | H | 3,4-methylene dioxyphenyl | C(O) | 3-(1,2,5-triazolyl) | 5-(3-pyridyl) |
| 98 | H | 3-trifluoro methyl-4-chlorophenyl | C(O) | 3-(1,2,5-triazolyl) | 1-phenyl-4-methyl |
| 99 | H | 4-cyano phenyl | C(O) | 3-(1,2,5-triazolyl) | 1-phenyl-4-methyl |
| 100 | H | 4-methoxy carbonyl phenyl | C(O) | 3-(1,2,5-triazolyl) | 1-phenyl-4-methyl |
| 101 | H | 4-methoxy phenyl | C(O) | 3-(1,2,5-triazolyl) | 1-phenyl-4-methyl |
| 102 | H | 4-nitrophenyl | C(O) | 3-(1,2,5-triazolyl) | 1-phenyl-4-methyl |
| 103 | dimethyl aminoethyl | 3,4-methylene dioxyphenyl | C(O) | 3-furyl | 2-methyl-5-(4-chloro phenyl) |
| 104 | H | 3,4-methylene dioxyphenyl | C(O) | 3-furyl | 2-methyl-5-phenyl |
| 105 | H | 3,4-methylene | C(O) | 3-furyl | 2-trifluoro |

TABLE 2-continued

| Cmpd # | R^D | R^2 | Y | C (ring) | R^3 |
|---|---|---|---|---|---|
| | | dioxyphenyl | | | methyl-5-(4-chlorophenyl) |
| 106 | H | 3,4-methylene dioxyphenyl | C(O) | 3-pyrazolyl | 1-phenyl-5-methyl |
| 107 | H | 4-[N-(3-di methylamino)-n-propoxy] phenyl | C(O) | 3-pyrazolyl | 1-phenyl-5-methyl |
| 108 | H | 3,4-methylene dioxyphenyl | C(O) | 3-pyridyl | 6-chloro |
| 109 | H | 3,4-dichloro phenyl | C(O) | 4-isoxazolyl | 3-phenyl-5-methyl |
| 110 | H | 3,4-dimethoxy phenyl | C(O) | 4-isoxazolyl | 3-phenyl-5-methyl |
| 111 | H | 3,4-dimethyl phenyl | C(O) | 4-isoxazolyl | 3-phenyl-5-methyl |
| 112 | H | 3,4-methylene dioxyphenyl | C(O) | 4-isoxazolyl | 3-phenyl-5-methyl |
| 113 | H | 3,5-dimethyl phenyl | C(O) | 4-isoxazolyl | 3-phenyl-5-methyl |
| 114 | H | 3-trifluoro methyl-4-chlorophenyl | C(O) | 4-isoxazolyl | 3-phenyl-5-methyl |
| 115 | H | 4-cyanophenyl | C(O) | 4-isoxazolyl | 3-phenyl-5-methyl |
| 116 | H | 4-methoxy carbonyl phenyl | C(O) | 4-isoxazolyl | 3-phenyl-5-methyl |
| 117 | H | 4-methoxy phenyl | C(O) | 4-isoxazolyl | 3-phenyl-5-methyl |
| 118 | H | 4-nitrophenyl | C(O) | 4-isoxazolyl | 3-phenyl-5-methyl |
| 119 | H | 3,4-dimethyl phenyl | C(O) | 4-pyrazolyl | 1-phenyl-5-trifluoromethyl |
| 120 | H | 3,4-dichloro phenyl | C(O) | 4-pyrazolyl | 1-phenyl-5-trifluoromethyl |
| 121 | H | 3,4-dimethoxy phenyl | C(O) | 4-pyrazolyl | 1-phenyl-5-trifluoromethyl |
| 122 | H | 3,4-methylene dioxyphenyl | C(O) | 4-pyrazolyl | 1-phenyl-5-n-propyl |
| 123 | H | 3,4-methylene dioxyphenyl | C(O) | 4-pyrazolyl | 1-phenyl-5-trifluoromethyl |
| 124 | H | 3,4-methylene dioxyphenyl | C(O) | 4-pyrazolyl | 1-(4-chloro phenyl)-5-trifluoromethyl |
| 125 | H | 3,4-methylene dioxyphenyl | C(O) | 4-pyrazolyl | 1-(4-nitrophenyl)-5-trifluoromethyl |
| 126 | H | 3,5-dimethyl phenyl | C(O) | 4-pyrazolyl | 1-phenyl-5-trifluoromethyl |
| 127 | H | 3-trifluoro methyl-4-chlorophenyl | C(O) | 4-pyrazolyl | 1-phenyl-5-trifluoromethyl |
| 128 | H | 4-cyanophenyl | C(O) | 4-pyrazolyl | 1-phenyl-5-trifluoromethyl |
| 129 | H | 4-methoxy carbonyl phenyl | C(O) | 4-pyrazolyl | 1-phenyl-5-trifluoromethyl |
| 130 | H | 4-methoxy phenyl | C(O) | 4-pyrazolyl | 1-phenyl-5-trifluoromethyl |
| 131 | H | 4-nitrophenyl | C(O) | 4-pyrazolyl | 1-phenyl-5-trifluoromethyl |
| 132 | H | 3,4-methylene | C(O) | 4-thiazolyl | 2-(4-pyrazinyl) |

TABLE 2-continued

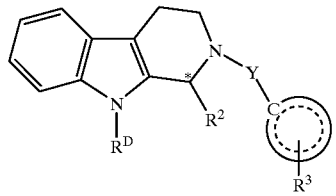

| Cmpd # | R<sup>D</sup> | R<sup>2</sup> | Y | Y ring | R<sup>3</sup> |
|---|---|---|---|---|---|
| | | dioxyphenyl | | | |
| 133 | H | 3,4-dichloro phenyl | C(O) | 5-pyrazolyl | 1-benzyl-3-t-butyl |
| 134 | H | 3,4-dimethoxy phenyl | C(O) | 5-pyrazolyl | 1-benzyl-3-t-butyl |
| 135 | H | 3,4-dimethyl phenyl | C(O) | 5-pyrazolyl | 1-benzyl-3-t-butyl |
| 136 | H | 3,4-methylene dioxyphenyl | C(O) | 5-pyrazolyl | 1-benzyl-3-t-butyl |
| 137 | H | 3,5-dimethyl phenyl | C(O) | 5-pyrazolyl | 1-benzyl-3-t-butyl |
| 138 | H | 3-trifluoro methyl-4-chlorophenyl | C(O) | 5-pyrazolyl | 1-benzyl-3-t-butyl |
| 139 | H | 4-cyanophenyl | C(O) | 5-pyrazolyl | 1-benzyl-3-t-butyl |
| 140 | H | 4-methoxy carbonyl phenyl | C(O) | 5-pyrazolyl | 1-benzyl-3-t-butyl |
| 141 | H | 4-methoxy phenyl | C(O) | 5-pyrazolyl | 1-benzyl-3-t-butyl |
| 142 | H | 4-nitrophenyl | C(O) | 5-pyrazolyl | 1-benzyl-3-t-butyl |
| 143 | dimethyl aminoethyl | 3,4-methylene dioxyphenyl | C(O) | napthyl | — |
| 144 | H | 3,4-methylene dioxyphenyl | C(O) | napthyl | — |
| 145 | H | 3,4-methylene dioxyphenyl | SO<sub>2</sub> | 2-thienyl | 5-phenyl sulfonyl |
| 146 | H | 3,4-methylene dioxyphenyl | SO<sub>2</sub> | 2-thienyl | 3-phenyl sulfonyl |
| 147 | dimethyl aminoethyl | 3,4-methylene dioxyphenyl | C(O) | 2-benzofuryl | — |
| 149 | H | 3,4-methylene dioxyphenyl | C(O) | 2-furyl | 5-phenyl |
| 152 | dimethyl aminoethyl | 3,4-methylene dioxyphenyl | C(O) | 2-furyl | 5-phenyl |
| 185 | H | 3,4-methylene dioxyphenyl | CH<sub>2</sub> | phenyl | — |

TABLE 3

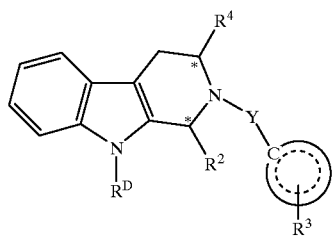

| Cmpd # | R<sup>2</sup> | R<sup>4</sup> | Y | Y ring | R<sup>3</sup> |
|---|---|---|---|---|---|
| 67 | 3,4-methylene dioxyphenyl | carboxy | C(O) | 2-furyl | 5-(3-nitro phenyl) |

TABLE 3-continued

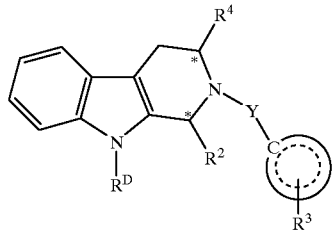

| Cmpd # | R² | R⁴ | Y | | R³ |
|---|---|---|---|---|---|
| 68 | 3,4-methylene dioxyphenyl | 2-(dimethyl amino)ethoxy carbonyl | C(O) | 2-furyl | 5-(3-nitro phenyl) |
| 69 | 3,4-methylene dioxyphenyl | 2-(dimethyl amino)ethyl aminocarbonyl | C(O) | 2-furyl | 5-(3-trifluoro methylphenyl) |
| 70 | 3,4-methylene dioxyphenyl | carboxy | C(O) | 2-furyl | 5-(3-trifluoro methylphenyl) |
| 71 | 3,4-methylene dioxyphenyl | methoxy carbonyl | C(O) | 2-furyl | 5-(3-trifluoro methylphenyl) |
| 72 | 3,4-methylene dioxyphenyl | methoxy carbonyl | C(O) | 2-furyl | 5-(3-trifluoro methylphenyl) |
| 73 | 3,4-methylene dioxyphenyl | methoxy carbonyl | C(O) | 2-furyl | 5-(3-nitro phenyl) |

TABLE 4

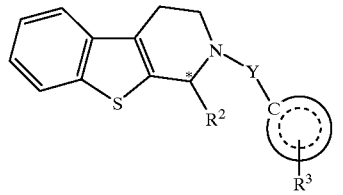

| Cmpd # | R² | Y | | R³ |
|---|---|---|---|---|
| 76 | 3,4-methylene dioxyphenyl | C(O) | 2-furyl | 5-(3-nitrophenyl) |
| 77 | 3,4-methylene dioxyphenyl | C(O) | 2-furyl | 5-(4-chlorophenyl) |

TABLE 5

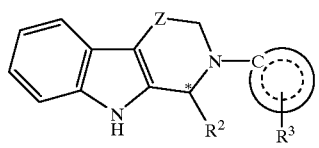

| Cmpd # | R² | Z | | R³ |
|---|---|---|---|---|
| 157 | 3,4-methylene dioxyphenyl | C(O) | 2-pyrimidinyl | 5-(3,4-dimethoxy phenyl) |
| 158 | 3,4-methylene dioxyphenyl | CHOH | 2-pyrimidinyl | 5-(3,4-dimethoxy phenyl) |

TABLE 5-continued

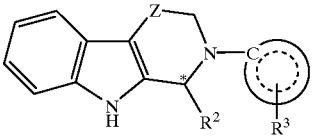

| Cmpd # | R² | Z | C | R³ |
|---|---|---|---|---|
| 159 | 3,4-methylene dioxyphenyl | C(O) | 2-pyrimidinyl | 5-(4-methylphenyl) |
| 160 | 3,4-methylene dioxyphenyl | CHOH | 2-pyrimidinyl | 5-(4-methylphenyl) |
| 162 | 3,4-methylene dioxyphenyl | C(O) | 2-pyrimidinyl | 5-(4-methoxyphenyl) |
| 163 | 3,4-methylene dioxyphenyl | C(O) | 2-pyrimidinyl | 5-(4-methoxyphenyl) |
| 164 | 3,4-methylene dioxyphenyl | CHOH | 2-pyrimidinyl | 5-(4-methoxyphenyl) |
| 165 | 3,4-methylene dioxyphenyl | C(O) | 2-pyrimidinyl | 5-(4-methoxyphenyl) |

EXAMPLE 10

IN VITRO TESTING

Cyclic Nucleotide Phosphodiesterase (PDE) Assay

PDEV Isolation

PDEV was isolated from rabbit and human tissues according to the protocol described by Boolell et al. (Boolell, M., Allen, M. J., Ballard, S. A., Ge[o-Attee, S., Muirhead, G. J., Naylor, A. M., Osterloh, I. H., and Gingell, C) in *International Journal of Impotence Research* 1996 8, 47–52 with minor modifications.

Briefly, rabbit or human tissues were homogenized in an ice-cold buffer solution containing 20 mM HEPES (pH 7.2), 0.25M sucrose,1 mM EDTA, and 1 mM phenylmethylsulphonyl fluoride (PMSF). The homogenates were centrifuged at 100,000 g for 60 minutes at 4° C. The supernatant was filtered through 0.2 μM filter and loaded on a Pharmacia Mono Q anion exchange column (1 ml bed volume) that was equilibrated with 20 mM HEPES, 1 mM EDTA and 0.5 mM PMSF. After washing out unbound proteins, the enzymes were eluted with a linear gradient of 100–600 mM NaCl in the same buffer (35 to 50 ml total, depending on the tissue. Enzymes from the skeletal muscle, corpus cavernosum, retina, heart and platelet were eluted with 35, 40, 45, 50, and 50 ml respectively.) The column was run at a flow rate of 1 ml/min and 1 ml fractions were collected. The fractions comprising various PDE activities were pooled separately and used in later studies.

Measurement of Inhibition of PDEV

The PDE assay was carried out as described by Thompson and Appleman in *Biochemistry* 1971 10, 311–316 with minor modifications, as noted below.

The assays were adapted to a 96-well format. The enzyme was assayed in 5 mM $MgCl_2$, 15 mM Tris HCl (pH 7.4), 0.5 mg/ml bovine serum albumin, 1 μM cGMP or cAMP, 0.1 μCi [$^3$H]-cGMP or [$^3$H]-cAMP, and 2–10 μl of column elution. The total volume of the assay was 100 μl. The reaction mixture was incubated at 30° C. for 30 minutes. The reaction was stopped by boiling for 1 minute and then cooled down on ice. The resulting [$^3$H] 5'-mononucleotides were further converted to uncharged [$^3$H]-nucleosides by adding 25 μl 1 mg/ml snake venom (Ophiophagus hannah) and incubating at 30° C. for 10 minute. The reaction was stopped by the addition of 1 ml Bio-Rad AG1-X2 resin slurry (1:3). All the charged nucleotides were bound by the resin and only the uncharged [$^3$H]-nucleosides remained in the supernatant after centrifuging. An aliquot of 200 μl was taken and counted by liquid scintillation. PDE activity was expressed as pmol cyclic nucleotide hydrolyzed/min/ml of enzyme preparation.

Inhibitor studies were carried out in assay buffer with a final concentration of 10% DMSO. Under these conditions, the hydrolysis of product increased with time and enzyme concentration in a linear fashion.

EXAMPLE 11

In Vitro Determination of $K_i$ for Phosphodiesterase Inhibitors

The assay was adapted to a 96-well format. Phosphodiesterase was assayed in 5 mM $MgCl_2$, 15 mM Tris HCl (pH 7.4), 0.5 mg/ml bovine serum albumin, 30 nM $^3$H-cGMP and test compound at various concentrations. The amount of enzyme used for each reaction was such that less than 15% of the initial substrate was converted during the assay period. For all measurements, the test compound was dissolved and diluted in 100% DMSO (2%DMSO in assay). The total volume of the assay was 100 μl. The reaction mixture was incubated at 30° C. for 90 minutes. The reaction was stopped by boiling for 1 minute and then immediately cooled by transfer to an ice bath. To each well was then added 25 μl 1 mg/ml snake venom (Ophiophagus hannah) and the reaction mixture incubating at 30° C. for 10 minute. The reaction was stopped by the addition of 1 ml Bio-Rad AG1-X2 resin slurry (1:3). An aliquot of 200 μl was taken and counted by liquid scintillation.

The % inhibition of the maximum substrate conversion (by the enzyme in the absence of inhibitor) was calculated for each test compound concentration. Using *GraphPad Prism's* nonlinear regression analysis (sigmoidal dose response), the % inhibition vs log of the test compound concentration was plotted to determine the $IC_{50}$. Under conditions where substrate concentration $<<K_m$ of the enzyme ($K_m$=substrate concentration at which half of the maximal velocity of the enzyme is achieved), $K_i$ is equivalent to the $IC_{50}$ value.

Mass spec and PDEV inhibitory activity for representative compounds of the present invention are described in Tables 6–7. Inhibitory data is presented either as the $IC_{50}$ ($\mu M$), as a percent inhibition at a given concentration of test compound or as a Ki value.

TABLE 6

| Cmpd # | MW | MS (M + 1) | % Inh @ 10 $\mu M$ (rabbit) |
|---|---|---|---|
| 1 | 288.30 | 289 | 67 |
| 2 | 496.63 | 497 | 43 |
| 3 | 425.51 | 426 | 84 |
| 4 | 552.08 | 553 | 94 |
| 5 | 577.68 | 578 | |
| 6 | 547.66 | 548 | 95 |
| 7 | 506.56 | 507 | 91 |
| 8 | 569.60 | 580 | 89 |
| 9 | 476.53 | 477 | 80 |
| 10 | 480.95 | 481 | 79 |
| 11 | 550.96 | 551 | 53 |
| 12 | 516.52 | 517 | 76 |
| 13 | 552.58 | 553 | 94 |
| 14 | 481.46 | 482 | 88 |
| 15 | 466.49 | 467 | 90 |
| 16 | 436.47 | 437 | 88 |
| 17 | 523.65 | 524 | 88 |
| 18 | 452.53 | 453 | 87 |
| 19 | 758.64 | 759 | 15 |
| 20 | 804.64 | 805 | 4 |
| 21 | 543.48 | 544 | 32 |
| 22 | 566.48 | 567 | 16 |
| 23 | 616.59 | 617 | 30 |
| 24 | 579.56 | 580 | 40 |
| 25 | 602.56 | 603 | 20 |
| 26 | 621.61 | 622 | 88 |
| 27 | 621.05 | 622 | 56 |
| 28 | 643.66 | 644 | 94 |
| 29 | 602.56 | 601* (M − 1) No M + 1 ion | 79 |
| 30 | 565.54 | 564 | 93 |
| 31 | 588.54 | 587* (M − 1) no M + 1 ion | 75 |
| 33 | 629.68 | 630 | 88 |
| 33 | 629.68 | 630 | 63 |
| 34 | 629.68 | 630 | 67 |
| 35 | 601.62 | 602 | 98 |
| 36 | 513.63 | 514 | 97 |
| 37 | 578.62 | 579 | 95 |
| 38 | 578.62 | 579 | 91 |
| 39 | 568.07 | 569 | 93 |
| 40 | 613.07 | 614 | 78 |
| 41 | 578.62 | 579 | 93 |
| 42 | 592.65 | 593 | 89 |
| 43 | 636.07 | 637 | 22 |
| 44 | 615.65 | 616 | 65 |
| 45 | 477.52 | 478 | |
| 46 | 496.95 | 497 | |
| 47 | 541.94 | 542 | 83 |
| 48 | 577.59 | 578 | 60 |
| 49 | 519.55 | 520 | 60 |
| 50 | 507.50 | 508 | 76 |
| 51 | 541.94 | 542 | |
| 52 | 577.59 | 578 | 76 |
| 53 | 521.53 | 522 | 85 |
| 54 | 507.50 | 508 | 81 |
| 55 | 519.55 | 520 | 70 |
| 56 | 507.50 | 508 | |
| 57 | 564.95 | 565 | 76 |
| 58 | 530.50 | 531 | |
| 59 | 477.52 | 478 | 92 |
| 60 | 549.62 | 550 | 89 |
| 61 | 562.62 | 563 | 90 |
| 62 | 454.40 | 455 | 86 |
| 63 | 465.30 | 465 | 78 |
| 64 | 431.40 | 432 | 83 |
| 65 | 442.51 | 443 | 66 |
| 66 | 541.94 | 542 | 23 |
| 67 | 550.50 | 549* (M − 1) No M + 1 ion | 50 |
| 68 | 622.63 | 623 | 35 |
| 69 | 644.65 | 645 | 21 |
| 70 | 574.51 | 573 | 46 |
| 71 | 588.54 | 587* (M − 1) No M + 1 ion | 21 |
| 72 | 588.54 | 587* (M − 1) No M + 1 ion | 15 |
| 73 | 565.54 | 564* (M − 1) No M + 1 ion | 20 |
| 74 | 621.61 | 622 | 84 |
| 75 | 627.66 | 628 | |
| 76 | 524.55 | 525 | 27 |
| 77 | 514.00 | 515 | 58 |
| 78 | 487.48 | 488 | 35 |
| 79 | 520.94 | 521 | 37 |
| 80 | 488.50 | 489 | 27 |
| 81 | 511.50 | 510* (M − 1) No M + 1 ion | 18 |
| 82 | 529.56 | 530 | 13 |
| 83 | 506.56 | 507 | 27 |
| 84 | 531.49 | 532 | 20 |
| 85 | 508.49 | 509 | 26 |
| 86 | 464.48 | 465 | 69 |
| 87 | 487.48 | 488 | 34 |
| 88 | 486.49 | 487 | 49 |
| 89 | 561.58 | 562 | |
| 90 | 546.57 | 547 | 69 |
| 91 | 513.01 | 514 | 82 |
| 92 | 461.57 | 462 | 39 |
| 93 | 502.40 | 503 | 44 |
| 94 | 493.56 | 494 | 19 |
| 95 | 461.57 | 462 | 13 |
| 96 | 477.52 | 478 | 57 |
| 97 | 480.55 | 481 | 71 |
| 98 | 535.95 | 536 | 38 |
| 99 | 458.52 | 459 | 40 |
| 100 | 491.55 | 492 | 24 |
| 101 | 463.54 | 464 | 48 |
| 102 | 478.51 | 479 | 40 |
| 103 | 510.97 | 511 | 55 |
| 104 | 476.53 | 477 | 72 |
| 105 | 564.95 | 565 | 40 |
| 106 | 476.53 | 477 | 70 |
| 107 | 533.67 | 534 | 15 |
| 108 | 431.88 | 432 | 48 |
| 109 | 502.40 | 503 | 31 |
| 110 | 493.56 | 494 | 32 |
| 111 | 461.56 | 462 | 35 |
| 112 | 477.52 | 478 | 33 |
| 113 | 461.56 | 462 | 29 |
| 114 | 535.95 | 536 | 27 |
| 115 | 458.52 | 459 | 30 |
| 116 | 491.54 | 492 | 32 |
| 117 | 463.53 | 464 | 32 |
| 118 | 478.51 | 479 | 28 |
| 119 | 514.55 | 515 | 28 |
| 120 | 555.39 | 556 | 18 |
| 121 | 546.55 | 547 | 10 |
| 122 | 504.59 | 505 | 65 |
| 123 | 530.50 | 531 | 56 |
| 124 | 564.95 | 565 | 53 |
| 125 | 575.50 | 576 | 54 |
| 126 | 514.55 | 515 | 12 |
| 127 | 588.94 | 589 | 13 |
| 128 | 511.51 | 512 | 11 |
| 129 | 544.53 | 545 | 46 |
| 130 | 516.52 | 517 | 45 |
| 131 | 531.49 | 532 | 12 |
| 132 | 480.55 | 481 | 76 |
| 133 | 557.52 | 556 | 1 |
| 134 | 548.68 | 547 | 5 |
| 135 | 516.69 | 517 | 8 |
| 136 | 532.64 | 533 | 18 |
| 137 | 516.69 | 517 | −3 |

TABLE 6-continued

| Cmpd # | MW | MS (M + 1) | % Inh @ 10 μM (rabbit) |
|---|---|---|---|
| 138 | 591.07 | 592 | 13 |
| 139 | 513.64 | 514 | −9 |
| 140 | 546.67 | 547 | 8 |
| 141 | 518.66 | 519 | 11 |
| 142 | 533.63 | 534 | −5 |
| 143 | 517.63 | 518 | 60 |
| 144 | 446.50 | 447 | 76 |
| 145 | 578.69 | 579* (M − 1) No M + 1 ion | 43 |
| 146 | 578.69 | 579 | 35 |

TABLE 7

| Cmpd # | MW | MS (M + 1) | $IC_{50}$ (μM) | % INH @ 10 μM (rabbit) |
|---|---|---|---|---|
| 147 | 507.59 | 508 | 5.2 | 52 |
| 148 | 573.69 | 574 | 4.4 | 66 |
| 149 | 462.50 | 463 | 0.75 | 80 |
| 150 | 526.55 | 527 |  | 4 |
| 151 | 409.44 | 410 | 0.13 | 95 |
| 152 | 533.63 | 534 | 1.2 | 80 |
| 153 | 447.50 | 448 | 0.12 | 95 |
| 154 | 666.76 | 667 | 0.11 | 97 |
| 155 | 480.56 | 481 | 9.2 | 57 |
| 156 | 518.62 | 519 | 0.0075 |  |
| 157 | 520.54 | 521 | 0.0087[a] |  |
| 158 | 522.56 | 523 |  | 49 |
| 159 | 474.52 | 475 | 0.024 |  |
| 160 | 476.53 | 477 | 8.95 |  |
| 161 | 460.54 | 461 | 0.789 |  |
| 162 | 490.52 | 491 | 0.024[a] |  |
| 164 | 492.53 | 493 |  | 82 |
| 166 | 628.73 | 629 |  | 58 |
| 167 | 522.60 | 523 | 1.49 |  |
| 168 | 370.41 | 371 | 2.15[a] |  |
| 169 | 481.57 | 482 | 0.042 |  |
| 170 | 451.55 | 452 | 0.049 |  |
| 172 | 408.46 | 409 |  | 44[a] |
| 174 | 474.56 | 475 | 0.150[a] |  |
| 175 | 506.56 | 507 | 0.214 |  |
| 176 | 506.56 | 507 | 0.056 |  |
| 178 | 557.70 | 558 |  | 37 |
| 179 | 449.31 | 450 | 1.58 |  |
| 180 | 573.69 | 574 |  | 40 |
| 182 | 445.52 | 446 | 0.058 |  |
| 183 | 447.50 | 448 | 0.122[a] |  |
| 184 |  |  | 0.640[a] |  |
| 185 |  | 446 |  | 200.40[a] |
| 186 |  | 448 |  | 240.10[2] |
| 187 |  | 446 |  | 49.79[a] |
| 188 |  | 491 |  | 642.69[a] |
| 189 |  | 448 |  | 121.60[a] |
| 190 |  | 463 |  | Ki = 14.21 nM |
| 191 |  | 443 |  | Ki = 0.69 nM |

[a]Compounds tested using human tissue.

EXAMPLE 12

IN VIVO TESTING

Following the procedure disclosed by Carter et al., (Carter, A. J., Ballard, S. A., and Naylor, A. M.) in The Journal of Urology 1998, 160, 242–246, compounds of the present invention are tested for in vivo efficacy.

EXAMPLE 13

As a specific embodiment of an oral composition, 100 mg of the compound of Example 7 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of the formula (I):

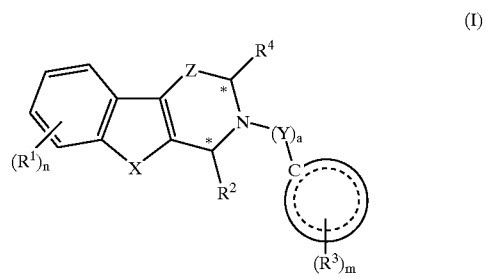

wherein
$R^1$ is independently selected from the group consisting of halogen, nitro, hydroxy, $C_1$–$C_8$alkyl, $C_1$–$C_8$alkoxy, —$NH_2$, —$NHR^A$, —$N(R^A)_2$, —O—$R^A$, —$C(O)NH_2$, —$C(O)NHR^A$, —$C(O)N(R^A)_2$, —$NC(O)$—$R^A$, —$SO_2NHR^A$, —$SO_2N(R^A)_2$, phenyl (optionally substituted with 1 to 3 $R^B$) and heteroaryl (optionally substituted with 1 to 3 $R^B$);

where each $R^A$ is independently is independently selected from the group consisting of $C_1$–$C_8$alkyl, aryl (optionally substituted with 1 to 3 $R^B$), $C_1$–$C_8$aralkyl (optionally substituted with 1 to 3 $R^B$) and heteroaryl (optionally substituted with 1 to 3 $R^B$);

where each $R^B$ is independently selected from the group consisting of halogen, hydroxy, nitro, cyano, $C_1$–$C_8$alkyl, $C_1$–$C_8$alkoxy, $C_1$–$C_8$alkoxycarbonyl, carboxy $C_1$–$C_8$alkyl, $C_1$–$C_8$alkylsulfonyl, trifluoromethyl, trifluoromethoxy, amino, acetylamino, di($C_1$–$C_8$alkyl)amino, di($C_1$–$C_8$alkyl)amino $C_1$–$C_8$alkoxy, di($C_1$–$C_8$alkyl) aminoacetyl $C_1$–$C_8$alkyl, di($C_1$–$C_8$alkyl)aminoacetylamino, carboxy$C_1$–$C_8$alkylcarbonylamino, hydroxy$C_1$–$C_8$alkylamino, $NHR^A$, $N(R^A)_2$ and heterocycloalkyl$C_1$–$C_8$alkoxy;

n is an integer from 0 to 4;

X is $NR^D$; where $R^D$ is selected from the group consisting of hydrogen, hydroxy, —$OR^A$, $C_1$–$C_8$alkyl (wherein the alkyl is optionally substituted with one to three substituent independently selected from halogen, carboxy, amino, $C_1$–$C_8$alkylamino, di($C_1$–$C_8$alkyl)amino, $C_1$–$C_8$alkoxycarbonyl, heteroaryl or heterocycloalkyl), heteroaryl and heteroarylcarbonyl (wherein the heteroaryl may be optionally substituted with phenyl or substituted phenyl, where the phenyl substituents are one to three $R^B$);

$R^2$ is selected from the group consisting of $C_5$–$C_{10}$alkyl (optionally substituted with 1 to 3 $R^C$), aryl (optionally substituted with 1 to 3 $R^B$), heteroaryl (optionally substituted with 1 to 3 $R^B$) and heterocycloalkyl (optionally substituted with 1 to 3 $R^B$);

where each $R^C$ is independently selected from the group consisting of halogen, hydroxy, nitro, $NH_2$, $NHR^A$ and $N(R^A)_2$;

Z is selected from the group consisting of $CH_2$, CHOH and C(O); provided that when Z is CHOH or C(O), then X is NH;

R⁴ is selected from the group consisting of hydrogen, hydroxy, carboxy, C₁–C₆alkylcarbonyl, C₁–C₆alkoxylcarbonyl, di(C₁–C₈alkyl)aminoalkoxycarbonyl, di(C₁–C₈alkyl)amino C₁–C₈alkylaminocarbonyl, and —COR^F;

where R^F is selected from the group consisting of C₁–C₈alkyl, NH₂, NHR^A, NR^A₂, —C₁–C₈alkyl—NH₂, —C₁–C₈alkyl—NHR^A, —C₁–C₈alkyl—NR^A₂ and —NH—C₁–C₈alkyl—NR^A₂;

a is an integer from 0 to 1;

Y is selected from the group consisting of CH₂, C(O), C(O)O, C(O)—NH and SO₂;

is selected from the group consisting of naphthyl and heteroaryl;

m is an integer from 0 to 2;

R³ is independently selected from the group consisting of halogen, nitro, C₁–C₈alkyl, C₁–C₈alkoxy, trifluoromethyl, trifluoromethoxy, phenyl (optionally substituted with 1 to 3 R^B), phenylsulfonyl, naphthyl, C₁–C₈aralkyl, heteroaryl (optionally substituted with 1 to 3 R^B), NH₂, NHR^A and N(R^A)₂;

provided that when

is 2-furyl or 2-thienyl, then m is an integer from 1 to 2;

and pharmaceutically acceptable salts thereof.

2. The compound of claim 1 wherein n is 0;

X is NR^D, wherein R^D is selected from the group consisting of hydrogen, haloC₁–C₆alkyl, di(C₁–C₄alkyl)aminoC₁–C₆alkyl, heteroaryl, heteroarylC₁–C₄alkyl, heterocycloalkyC₁–C₄alkyl, carboxyC₁–C₄alkyl, C₁–C₄alkoxycarbonylC₁–C₄alkyl and heteroarylcarbonyl; wherein the heteroaryl is further optionally substituted with phenyl or substituted phenyl, wherein the substituents on the phenyl are one to two independently selected from R^B;

where each R^B is independently selected from the group consisting of halogen, nitro, C₁–C₄alkyl, C₁–C₄alkoxy, trifluoromethyl, trifluoromethoxy, amino and di(C₁–C₄alkyl)amino;

R² is selected from the group consisting of 3,4-methylenedioxyphenyl, 3,4-(difluoro)methylenedioxyphenyl, 2,3-dihydrobenzofuryl, 2,3-dihydrobenzo-[1,4]-dioxin-6-yl, pyridyl, phenyl and substituted phenyl; wherein the phenyl substituents are one to two substituents independently selected from halogen, C₁–C₄alkyl, C₁–C₄alkoxy, trifluoromethyl, cyano, nitro, C₁–C₄alkoxycarbonyl, di(C₁–C₄alkyl)amino or di(C₁–C₄alkyl)aminoC₁–C₄alkoxy;

R⁴ is selected from the group consisting of hydrogen, carboxy, C₁–C₄alkoxycarbonyl, di(C₁–C₄alkyl)aminoC₁–C₄alkoxycarbonyl and di(C₁–C₄alkyl)aminoC₁–C₄alkylaminocarbonyl;

Y is selected from the group consisting of C(O), SO₂ and CH₂;

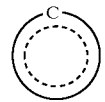

is selected from the group consisting of naphthyl and heteroaryl;

R³ is independently selected from the group consisting of halogen, nitro, C₁–C₄alkyl, C₁–C₄alkoxy, trifluoromethyl, C₁–C₄aralkyl, pyrazinyl, pyridyl, halogen substituted pyridyl, dimethyl substituted imidazolyl, phenyl, phenylsulfonyl and substituted phenyl; wherein the substituents on the phenyl are one or more substituents independently selected from halogen, hydroxy, C₁–C₄alkyl, C₁–C₄alkoxy, trifluoromethyl, trifluoromethoxy, nitro, amino, acetylamino, C₁–C₄alkylsulfonyl, carboxyC₁–C₄alkylcarbonylamino, hydroxyC₁–C₄alkylamino, di(C₁–C₄alkyl)aminoC₁–C₄alkoxy, di(C₁–C₄alkyl)aminoacetylamino or heterocycloalkylC₁–C₄alkoxy;

provided that when

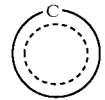

is 2-furyl or 2-thienyl, then m is an integer from 1 to 2;

and pharmaceutically acceptable salts thereof.

3. The compound of claim 2, wherein

X is NR^D, where R^D is selected from the group consisting of hydrogen, di(methyl)aminoethyl, di(methyl)amino-n-propyl, di(ethyl)aminoethyl, di(ethyl)amino-n-butyl, N-pyrrolidinylethyl, N-morpholinylethyl, 2-pyridylmethyl, 4-pyridylmethyl, 5-(4-methylphenyl)-2-pyrimidinyl, carboxymethyl, carboxyethyl, 4-chloro-n-butyl, 2-(5-(3-trifluoromethylphenyl)furyl)carbonyl, 2-(5-(3-nitrophenyl)furyl)carbonyl, methoxycarbonylmethyl, methoxycarbonylethyl and 2-benzoxazolyl;

R² is selected from the group consisting of phenyl, 3,4-methylenedioxyphenyl, 3,4-(difluoro)methylenedioxyphenyl, 2,3-dihydrobenzofuryl, 2,3-dihydrobenzo-[1,4]-dioxin-6-yl, 4-pyridyl, 3-pyridyl, 4-cyanophenyl, 3-nitrophenyl, 4-nitrophenyl, 4-trifluoromethylphenyl, 4-methoxyphenyl, 3,4-dimethylphenyl, 3,5-dimethylphenyl, 3,4-dimethoxyphenyl, 3-trifluoromethyl-4-chlorophenyl, 3,4-dichlorophenyl, 4-chlorophenyl, 4-methoxycarbonylphenyl, 3,4-dimethoxyphenyl, 4-(dimethylamino)phenyl and 4-(N-(3-dimethylamino)-n-propoxy)phenyl;

R⁴ is selected from the group consisting of hydrogen, carboxy, dimethylaminoethoxycarbonyl, dimethylaminoethylaminocarbonyl and methoxycarbonyl;

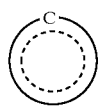

is selected from the group consisting of naphthyl, 2-pyrimidinyl, 2-furyl, 3-furyl, 2-benzofuryl, 2-theinyl, 2-benzothienyl, 2-benzothiazolyl, 2-benzoxazolyl, 2-benzimidazolyl, 4-thiazolyl, 2-thiazolyl, 3-pyrazolyl, 4-pyrazolyl, 5-pyrazolyl, 3-(1,2,5-triazolyl), 4-isoxazolyl, 2-pyridyl and 3-pyridyl;

$R^3$ is independently selected from the group consisting of chloro, bromo, methyl, n-propyl, t-butyl, methoxy, trifluoromethyl, nitro, phenyl, benzyl, phenylsulfonyl, 4-hydroxyphenyl, 4-chlorophenyl, 4-methylphenyl, 3,4-dimethoxyphenyl, 3-trifluoromethylphenyl, 4-trifluoromethylphenyl, 5-trifluoromethylphenyl, 4-methoxyphenyl, 2-nitrophenyl, 3-nitrophenyl, 4-nitrophenyl,3-aminophenyl, 4-aminophenyl, 2-nitro-4-chlorophenyl, 2-nitro-4-methylphenyl, 2-nitro-4-methylsulfonylphenyl, 3-acetylaminophenyl, 4-acetylaminophenyl, 4-(3-carboxy-n-propyl)carbonylaminophenyl, 2-chloro-5-trifluoromethylphenyl, 4-(4-hydroxy-n-butyl)aminophenyl, 2-(dimethylamino)acetylaminophenyl, 4-[2-(N-pyrrolidinyl)ethoxy]phenyl, 4-[2-(4-morpholinyl)ethoxy]phenyl, 4-(2-(dimethylamino)ethoxy)phenyl, 4-pyrazinyl, 2,3-dimethyl-3H-imidazolyl, 2-pyridyl and 3-pyridyl;

provided that when

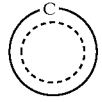

is 2-furyl or 2-thienyl, then m is an integer from 1 to 2;
and pharmaceutically acceptable salts thereof.

4. The compound of claim 3 wherein
X is $NR^D$, where $R^D$ is selected from the group consisting of hydrogen, di(methyl)aminoethyl, 4-pyridylmethyl, 2-pyridylmethyl, N-morpholinylethyl, carboxyethyl, carboxymethyl, di(ethyl)aminoethyl, N-pyrrolidinylethyl and 5-(4-methylphenyl)-2-pyrimidinyl;

$R^2$ is selected from the group consisting of 3,4-methylenedioxyphenyl, 2,3-dihydrobenzofuryl and 2,3-dihydrobenzo-[1,4]-dioxin-6-yl;

$R^4$ is hydrogen;

Y is selected from the group consisting of C(O) and $CH_2$;

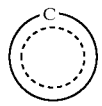

is selected from the group consisting of naphthyl, 2-pyrimidinyl, 2-furyl, 2-benzofuryl, 2-thienyl, 2-benzothienyl, 2-benzothiazolyl, 2-benzoxazolyl, 2-thiazolyl, 4-thiazolyl and 2-pyridyl;

m is an integer from 0 to 1;

$R^3$ is selected from the group consisting of bromo, t-butyl, methoxy, trifluoromethyl, nitro, phenyl, 4-chlorophenyl, 3,4-dimethoxyphenyl, 3-trifluoromethylphenyl, 4-methylphenyl, 4-methoxyphenyl, 2-nitrophenyl, 3-nitrophenyl, 4-nitrophenyl, 3-aminophenyl, 2-nitro-4-chlorophenyl, 2-nitro-4-methylphenyl, 2-nitro-4-methylsulfonylphenyl, 4-(3-carboxy-n-propyl)carbonylaminophenyl, 2-chloro-5-trifluoromethylphenyl, 4-(4-hydroxy-n-butyl)aminophenyl, 2-2-(dimethylamino)acetylaminophenyl, 4-pyrazinyl 2-pyridyl and 2,3-dimethyl-3H-imidazol-4-yl;

provided that when

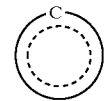

is 2-furyl or 2-thienyl, then m is 1;
and pharmaceutically acceptable salts thereof.

5. The compound of claim 4 wherein
X is $NR^D$, where $R^D$ is selected from the group consisting of hydrogen, di(methyl)aminoethyl, N-morpholinylethyl, carboxymethyl and N-pyrrolidinylethyl;

$R^2$ is selected from the group consisting of 3,4-methylenedioxyphenyl and 2,3-dihydrobenzofuryl;

Z is selected from the group consisting of $CH_2$ and C(O); provided that when Z is C(O), then X is NH;

Y is C(O);

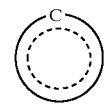

is selected from the group consisting of 2-pyrimidinyl, 2-furyl, 2-benzofuryl, 2-benzoxazolyl, 2-thiazolyl and 2-pyridyl;

$R^3$ is selected from the group consisting of t-butyl, methoxy, nitro, phenyl, 4-chlorophenyl, 4-methylphenyl, 4-methoxyphenyl, 3,4-dimethoxyphenyl, 3-trifluoromethylphenyl, 2-nitrophenyl, 3-nitrophenyl, 4-nitrophenyl, 3-aminophenyl, 2-nitro-4-methylsulfonylphenyl, 2-(dimethylamino)acetylaminophenyl, 2-pyridyl and 2,3-dimethyl-3H-imidazol-4-yl;

provided that when

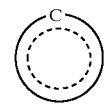

is 2-furyl, then m is 1;
and pharmaceutically acceptable salts thereof.

6. A compound of claim 3 selected from the group consisting of
1-(3,4-methylenedioxyphenyl)-2-[(5-phenyl-2-furyl)carbonyl]-2,3,4,9-tetrahydro-1H-β-carboline;
1-(3,4-methylenedioxyphenyl)-2-[5-(2-pyridyl)-2-pyrimidinyl]-9-di(methyl)aminoethyl-2,3,4,9-tetrahydro-1H-β-carboline;

1-(3,4-methylenedioxyphenyl)-2-[5-(3,4-dimethoxyphenyl)-2-pyrimidinyl]-1,2,3,9-tetrahydro-4-oxo-4H-β-carboline
1-(3,4-methylenedioxyphenyl)-2-[5-(4-methylphenyl)-2-pyrimidinyl]-1,2,3,9-tetrahydro-4-oxo-4H-β-carboline;
1-(3,4-methylenedioxyphenyl)-2-[5-(4-methoxyphenyl)-2-pyrimidinyl]-1,2,3,4-tetrahydro-4-oxo-4H-β-carboline;
1-(3,4-methylenedioxyphenyl)-2-[4-(4-methoxyphenyl)-2-thiazolyl]-2,3,4,9-tetrahydro-1H-β-carboline;
1-(3,4-methylenedioxyphenyl)-2-(4-phenyl-2-thiazolyl)-2,3,4,9-tetrahydro-1H-β-carboline;
2-[2,3']Bipyridinyl-6'-yl-1-(2,3-dihydro-benzofuran-5-yl)-2,3,4,9-tetrahydro-1H-β-carboline;
1-(2,3-dihydrobenzofuran-5-yl)-2-[5-(2,3-dimethyl-3H-imidazol-4-yl)-2,3-2,3,49-tetrahydro-1h-β-carboline;and pharmaceutically acceptable salts thereof.

7. A pharmaceutical composition comprising a pharmaceutically acceptable carrier and a compound of claim 1.

8. A pharmaceutical composition made by mixing a compound of claim 1 and a pharmaceutically acceptable carrier.

9. A method of treating sexual dysfunction in a subject in need thereof comprising administering to the subject a therapeutically effective amount of the compound of claim 1.

10. The method of treating sexual dysfunction of claim 9, wherein the sexual dysfunction is male erectile dysfunction.

11. The method of claim 9, wherein the sexual dysfunction is selected from the group consisting of male sexual dysfunction, male erectile dysfunction, impotence, female sexual dysfunction, female sexual arousal dysfunction and female sexual dysfunction related to blood flow and nitric oxide production in the tissues of the vagina and clitoris.

12. A method for increasing the concentration of cGMP in penile tissue in a male subject in need thereof comprising administering to the subject an effective amount of the compound of claim 1.

13. A method of treating a condition selected from the group consisting of male erectile dysfunction (ED), impotence, female sexual arousal dysfunction, female sexual dysfunction related to blood flow and nitric oxide production in the tissues of the vagina and clitoris, premature labor, dysmenorhea, cardiovascular disorders, atherosclerosis, arterial occlusive disorders, thrombosis, coronary rest stenosis, angina pectoris, myocardial infarction, heart failure, ischemic heart disorders, hypertension, pulmonary hypertension, asthma, intermittent claudication and diabetic complications in a subject in need thereof comprising administering to the subject a therapeutically effective amount of the compound of claim 1.

14. A process for making a pharmaceutical composition comprising mixing a compound of claim 1 and a pharmaceutically acceptable carrier.

* * * * *